(12) United States Patent
Cao

(10) Patent No.: US 11,273,433 B2
(45) Date of Patent: Mar. 15, 2022

(54) SINGLE-ATOM-BASED CATALYST SYSTEMS

(71) Applicant: University of Florida Research Foundation, Inc., Gainesville, FL (US)

(72) Inventor: Yunwei Charles Cao, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 17/177,901

(22) Filed: Feb. 17, 2021

(65) Prior Publication Data

US 2021/0187489 A1 Jun. 24, 2021

Related U.S. Application Data

(63) Continuation-in-part of application No. PCT/US2019/047233, filed on Aug. 20, 2019.

(Continued)

(51) Int. Cl.
*B01J 35/00* (2006.01)
*B33Y 80/00* (2015.01)
(Continued)

(52) U.S. Cl.
CPC ........... *B01J 35/0006* (2013.01); *B01J 21/08* (2013.01); *B01J 23/02* (2013.01); *B01J 23/10* (2013.01);
(Continued)

(58) Field of Classification Search
CPC ...... B01J 35/0006; B01J 35/002; B01J 21/08; B01J 23/02; B01J 23/10; B01J 23/30; B01J 23/34; B01J 23/745; B01J 23/755; B01J 23/83; B01J 35/0013; B01J 35/006; B01J 35/008; B01J 35/023; B01J 37/0009; B01J 37/0211; B01J 37/14; B33Y 80/00;
(Continued)

(56) References Cited

U.S. PATENT DOCUMENTS

2003/0083194 A1 5/2003 Sung
2003/0204111 A1 10/2003 Chaturvedi et al.
(Continued)

OTHER PUBLICATIONS

Jones, Matthew R., Nadrian C. Seeman, and Chad A. Mirkin. "Programmable materials and the nature of the DNA bond." Science 347.6224 (2015).
(Continued)

*Primary Examiner* — Youngsul Jeong
*Assistant Examiner* — Jason Y Chong
(74) *Attorney, Agent, or Firm* — Thomas | Horstemeyer, LLP

(57) ABSTRACT

The disclosure relates to a single-atom-based catalyst system with total-length control of single-atom catalytic sites. The single-atom-based catalyst system comprises at least one catalyst structure comprising a first assembly of a plurality of single-atom-catalyst superparticles. The single-atom-catalyst superparticles comprise a second assembly of a plurality of single-atom-catalyst nanoparticles. The single-atom-based catalyst system has controlled porosity and spatial distribution of active single-atom catalysts from the atomic scale to the macroscopic scale. This abstract is intended as a scanning tool for purposes of searching in the particular art and is not intended to be limiting of the present disclosure.

18 Claims, 14 Drawing Sheets

Related U.S. Application Data

(60) Provisional application No. 62/719,848, filed on Aug. 20, 2018.

(51) Int. Cl.

| | |
|---|---|
| B01J 21/08 | (2006.01) |
| B01J 23/02 | (2006.01) |
| B01J 23/10 | (2006.01) |
| B01J 23/30 | (2006.01) |
| B01J 23/34 | (2006.01) |
| B01J 23/745 | (2006.01) |
| B01J 23/755 | (2006.01) |
| B01J 35/02 | (2006.01) |
| B01J 37/00 | (2006.01) |
| B01J 37/02 | (2006.01) |
| B01J 37/14 | (2006.01) |
| C07C 2/84 | (2006.01) |
| C07C 5/48 | (2006.01) |
| B33Y 10/00 | (2015.01) |
| B29C 64/165 | (2017.01) |
| B28B 1/00 | (2006.01) |

(52) U.S. Cl.
CPC ............. *B01J 23/30* (2013.01); *B01J 23/34* (2013.01); *B01J 23/745* (2013.01); *B01J 23/755* (2013.01); *B01J 35/008* (2013.01); *B01J 35/023* (2013.01); *B01J 37/0009* (2013.01); *B01J 37/0211* (2013.01); *B01J 37/14* (2013.01); *B33Y 80/00* (2014.12); *C07C 2/84* (2013.01); *C07C 5/48* (2013.01); *B28B 1/001* (2013.01); *B29C 64/165* (2017.08); *B33Y 10/00* (2014.12); *C07C 2521/08* (2013.01); *C07C 2523/02* (2013.01); *C07C 2523/10* (2013.01); *C07C 2523/30* (2013.01); *C07C 2523/34* (2013.01); *C07C 2523/745* (2013.01); *C07C 2523/755* (2013.01)

(58) Field of Classification Search
CPC .. B33Y 10/00; C07C 2/84; C07C 5/42; C07C 5/48; C07C 2521/04; C07C 2521/06; C07C 2521/08; C07C 2521/10; C07C 2521/18; C07C 2523/02; C07C 2523/04; C07C 2523/06; C07C 2523/10; C07C 2523/14; C07C 2523/30; C07C 2523/34; C07C 2523/42; C07C 2523/745; C07C 2523/755; C07C 2523/78; C07C 2523/80; C07C 2523/83; B28B 1/001; B29C 64/165; Y02P 20/52

See application file for complete search history.

(56) References Cited

U.S. PATENT DOCUMENTS

| | | |
|---|---|---|
| 2010/0055462 A1 | 3/2010 | Cao |
| 2011/0150938 A1 | 6/2011 | Cao et al. |
| 2012/0302437 A1 | 11/2012 | Yang et al. |
| 2016/0208360 A1 | 7/2016 | Sun et al. |

OTHER PUBLICATIONS

Boles, Michael A., Michael Engel, and Dmitri V. Talapin. "Self-assembly of colloidal nanocrystals: from intricate structures to functional materials." Chemical reviews 116.18 (2016): 11220-11289.
Wang, Tie, et al. "Colloidal superparticles from nanoparticle assembly." Chemical Society Reviews 42.7 (2013): 2804-2823.
Wang, Tie, et al. "Self-assembled colloidal superparticles from nanorods." Science 338.6105 (2012): 358-363.
Yang, Yuchi, et al. "Scalable assembly of crystalline binary nanocrystal superparticles and their enhanced magnetic and electrochemical properties." Journal of the American Chemical Society 140.44 (2018): 15038-15047.
Bai, Feng, et al. "A versatile bottom-up assembly approach to colloidal spheres from nanocrystals." Angewandte Chemie 119.35 (2007): 6770-6773.
Zhuang, Jiaqi, et al. "Supercrystalline colloidal particles from artificial atoms." Journal of the American Chemical Society 129.46 (2007): 14166-14167.
Zhuang, Jiaqi, et al. "Controlling colloidal superparticle growth through solvophobic interactions." Angewandte Chemie International Edition 47.12 (2008): 2208-2212.
Zhuang, Jiaqi, et al. "Cylindrical superparticles from semiconductor nanorods." Journal of the American Chemical Society 131.17 (2009): 6084-6085.
Lacava, Johann, Philip Born, and Tobias Kraus. "Nanoparticle clusters with Lennard-Jones geometries." Nano letters 12.6 (2012): 3279-3282.
Wang, Tie, et al. "Shape-controlled synthesis of colloidal superparticles from nanocubes." Journal of the American Chemical Society 134.44 (2012): 18225-18228.
De Nijs, Bart, et al. "Entropy-driven formation of large icosahedral colloidal clusters by spherical confinement." Nature materials 14.1 (2015): 56-60.
Li, Peng, Qing Peng, and Yadong Li. "Dual-mode luminescent colloidal spheres from monodisperse rare-earth fluoride nanocrystals." Advanced Materials 21.19 (2009): 1945-1948.
Wang, Da, et al. "Interplay between spherical confinement and particle shape on the self-assembly of rounded cubes." Nature communications 9.1 (2018): 1-10.
Chen, Ou, et al. "Magneto-fluorescent core-shell supernanoparticles." Nature communications 5.1 (2014): 1-8.
Wang, Peng-peng, et al. "Colloidal binary supracrystals with tunable structural lattices." Journal of the American Chemical Society 140.29 (2018): 9095-9098.
Wang, Junwei, et al. "Magic number colloidal clusters as minimum free energy structures." Nature communications 9.1 (2018): 1-10.
Shi, Run, et al. "Self-assembled Au/CdSe nanocrystal clusters for plasmon-mediated photocatalytic hydrogen evolution." Advanced Materials 29.27 (2017): 1700803.
Wang, Junwei, et al. "Free energy landscape of colloidal clusters in spherical confinement." ACS nano 13.8 (2019): 9005-9015.
Wang, Da, et al. "Binary icosahedral clusters of hard spheres in spherical confinement." Nature Physics 17.1 (2021): 128-134.
Dong, Angang, et al. "Binary nanocrystal superlattice membranes self-assembled at the liquid-air interface." Nature 466.7305 (2010): 474-477.
Mackay, Alan Lindsay. "A dense non-crystallographic packing of equal spheres." Acta Crystallographica 15.9 (1962): 916-918.
Hofmeister, H. "Fivefold twinned nanoparticles." Encyclopedia of nanoscience and nanotechnology. Vol. 3. No. 452. Stevenson Ranch: American Scientific Publishers, 2004. 431-452.
Landman, Uzi, and W. D. Luedtke. "Small is different: energetic, structural, thermal, and mechanical properties of passivated nanocluster assemblies." Faraday discussions 125 (2004): 1-22.
Langille, Mark R., et al. "Stepwise evolution of spherical seeds into 20-fold twinned icosahedra." Science 337.6097 (2012): 954-957.
Hubert, Hervé, et al. "Icosahedral packing of B 12 icosahedra in boron suboxide (B 6 O)." Nature 391.6665 (1998): 376-378.
Frank, Frederick Charles. "Supercooling of liquids." Proceedings of the Royal Society of London. Series A. Mathematical and Physical Sciences 215.1120 (1952): 43-46.
Taffs, Jade, and C. Patrick Royall. "The role of fivefold symmetry in suppressing crystallization." Nature communications 7.1 (2016): 1-7.
Wang, Liangbing, et al. "Atomic-level insights in optimizing reaction paths for hydroformylation reaction over Rh/CoO single-atom catalyst." Nature communications 7.1 (2016): 1-8.
Lanzafame, Paola, et al. "Grand challenges for catalysis in the Science and Technology Roadmap on Catalysis for Europe: moving ahead for a sustainable future." Catalysis Science & Technology 7.22 (2017): 5182-5194.

(56) References Cited

OTHER PUBLICATIONS

Ge, Huibin, et al. "A tandem catalyst with multiple metal oxide interfaces produced by atomic layer deposition." Angewandte Chemie 55.25 (2016): 7081-7085.

Leitch, David C., et al. "Upgrading light hydrocarbons via tandem catalysis: a dual homogeneous Ta/Ir system for alkane/alkene coupling." Journal of the American Chemical Society 135.28 (2013): 10302-10305.

Xie, Chenlu, et al. "Tandem catalysis for CO2 hydrogenation to C2-C4 hydrocarbons." Nano letters 17.6 (2017): 3798-3802.

Li, Xinle, et al. "Tandem catalysis by palladium nanoclusters encapsulated in metal-organic frameworks." ACS Catalysis 4.10 (2014): 3490-3497.

Alobaidi, Fahad, Zhibin Ye, and Shiping Zhu. "Direct synthesis of linear low-density polyethylene of ethylene/1-hexene from ethylene with a tandem catalytic system in a single reactor." Journal of Polymer Science Part A: Polymer Chemistry 42.17 (2004): 4327-4336.

Karakaya, Canan, and Robert J. Kee. "Progress in the direct catalytic conversion of methane to fuels and chemicals." Progress in Energy and Combustion Science 55 (2016): 60-97.

Galadima, Ahmad, and Oki Muraza. "Revisiting the oxidative coupling of methane to ethylene in the golden period of shale gas: A review." Journal of Industrial and Engineering Chemistry 37 (2016): 1-13.

https://www.pmewswire.com/news-releases/global-ethylene-capacity-and-capital-expenditure-outlook—us-and-china-to-lead-ethylene-industry-expansion-300324140.html.

http://www.shell.com/energy-and-innovation/natural-gas/gas-to-liquids.html.

https://www.sasol.com/innovation/gas-liquids/overview.

https://www.icis.com/explore/resources/news/2007/11/05/9075777/ethylene-uses-and-market-data/.

http://www.essentialchemicalindustry.org/chemicals/ethene.html.

http://www.essentialchemicalindustry.org/processes/cracking-isomerisation-and-reforming.html#steam_cracking.

http://www.eia.gov/naturalgas/.

G.E. Keller, M.M. Bhasin, "Synthesis of Ethylene via Oxidative Coupling of Methane," Journal of Catalysis 73 (1982) 9-19.

K. Otsuka, K. Jinno, A. Morikawa, "Active and Selective Catalysts for the Synthesis of C2H4 and C2H6 via Oxidative Coupling of Methane," Journal of Catalysis 100 (1986).

T. Ito, J.H. Lunsford, "Synthesis of ethylene and ethane by partial oxidation of methane over lithium-doped magnesium oxide," Nature 314 (1985) 721-722.

Trenton W. Elkins, Björn Neumann, Marcus Bäumer, and Helena E. Hagelin-Weaver, "Effects of Li Doping on MgO-Supported Sm2O3 and TbOx Catalysts in the Oxidative Coupling of Methane," ACS Catalysis, 4 (2014) 1972-1990.

Trenton W. Elkins, Samantha J. Roberts, Helena E. Hagelin-Weaver, "Effects of alkali and alkaline-earth metal dopants on magnesium oxide supported rare-earth oxide catalysts in the oxidative coupling of methane," Applied Catalysis A 528 (2016) 175-190.

T.W. Elkins, H.E. Hagelin-Weaver, "Characterization of Mn—Na2WO4/SiO2 and Mn—Na2WO4/MgO catalysts for the oxidative coupling of methane," Applied Catalysis A 497 (2015) 96-106.

International Search Report and Written Opinion for PCT/US2019/047233 dated Nov. 15, 2019.

X. Guo, G. Fang, G. Li, et al. "Direct, Nonoxidative Conversion of Methane to Ethylene, Aromatics, and Hydrogen," Science 344 (2014) 616-619.

S.F. Hakonsen, J.C. Walmsley, A. Holmen, "Ethene production by oxidative dehydrogenation of ethane at short contact times over Pt-Sn coated monoliths," Applied Catalysis A 378 (2010) 1-10.

P.D.K. Nezhad, M. Haghighi, N. Jodeiri, F.Rahmani, "Sol-gel preparation of NiO/ZrO2(x)—MgO(100-x) nanocatalyst used in CO2/O2 oxidative dehydrogenation of ethane to ethylene: influence of Mg/Zr ratio on catalytic performance," Journal of Sol-Gel Science and Technology 80 (2016) 436-450.

H. Zhu, D.C. Rosenfeld, M. Harb, D.H. Anjum, M.N. Hedhili, S. Ould-Chikh, and J.-M. Basset, "Ni—M—O (M = Sn, Ti, W) Catalysts Prepared by a Dry Mixing Method for Oxidative Dehydrogenation of Ethane," ACS Catalysis, 6 (2016) 2852-2866.

J. Lynch, J. Zhuang, T. Wang, D. LaMontagne, H. Wu, and Y. C. Cao, Gas-Bubble Effects on the Formation of Colloidal Iron Oxide Nanocrystals J. Am. Chem. Soc., 133 (2011), 12664-12674.

J. Park, K. An, Y. Hwang, J. Park, H. Noh, J. Kim, J. Park, N. Hwang and T. Hyeon, Ultra-large-scale syntheses of monodisperse nanocrystals, Nature Materials, 3(2004), 891-895.

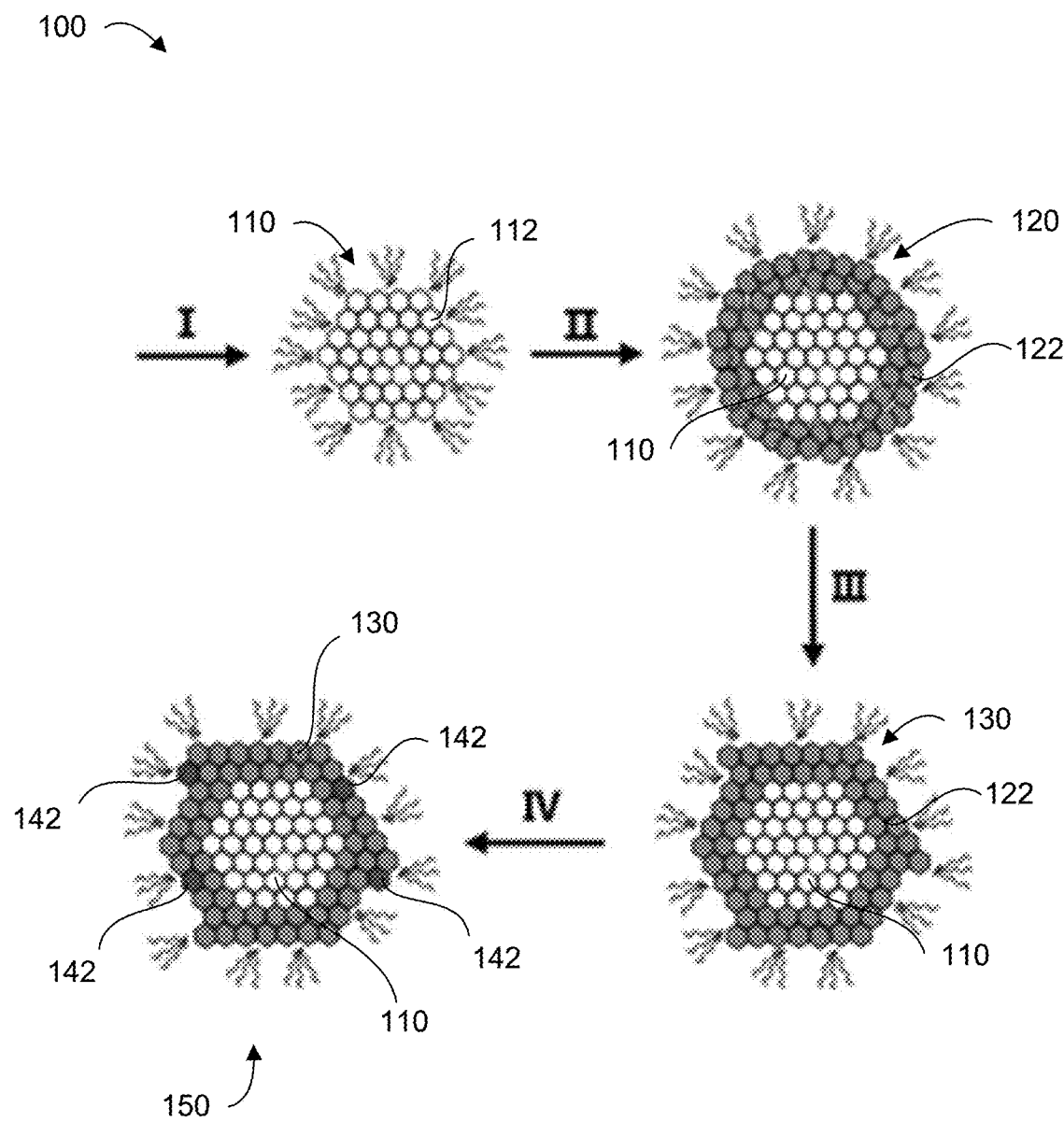
FIG. 1.1

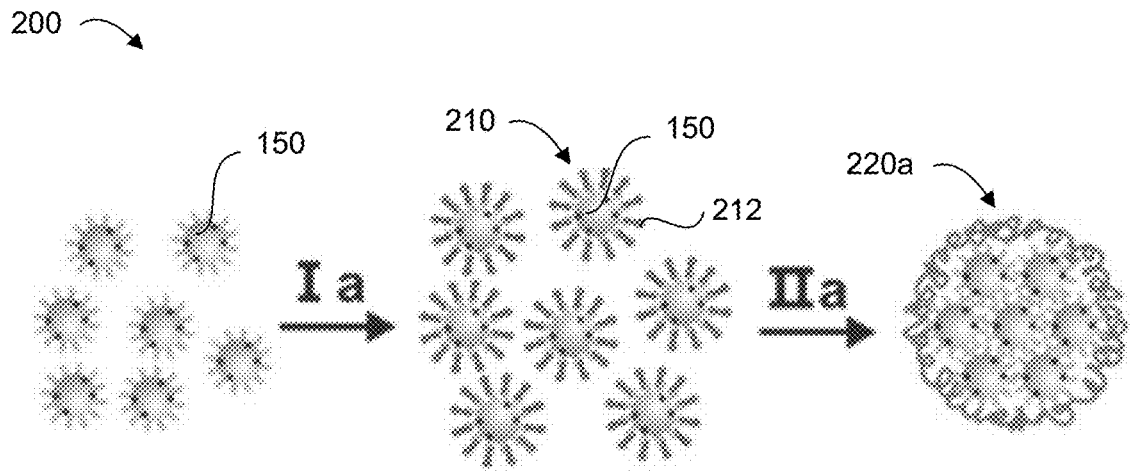
FIG. 1.2A
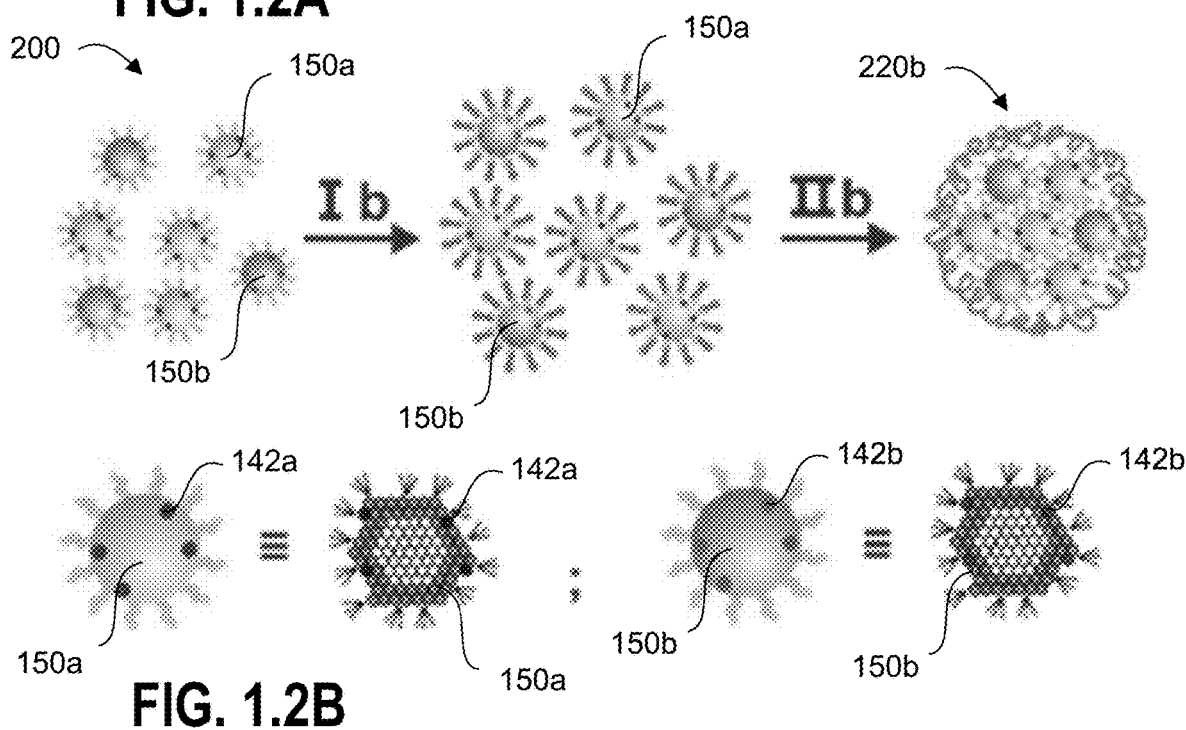
FIG. 1.2B

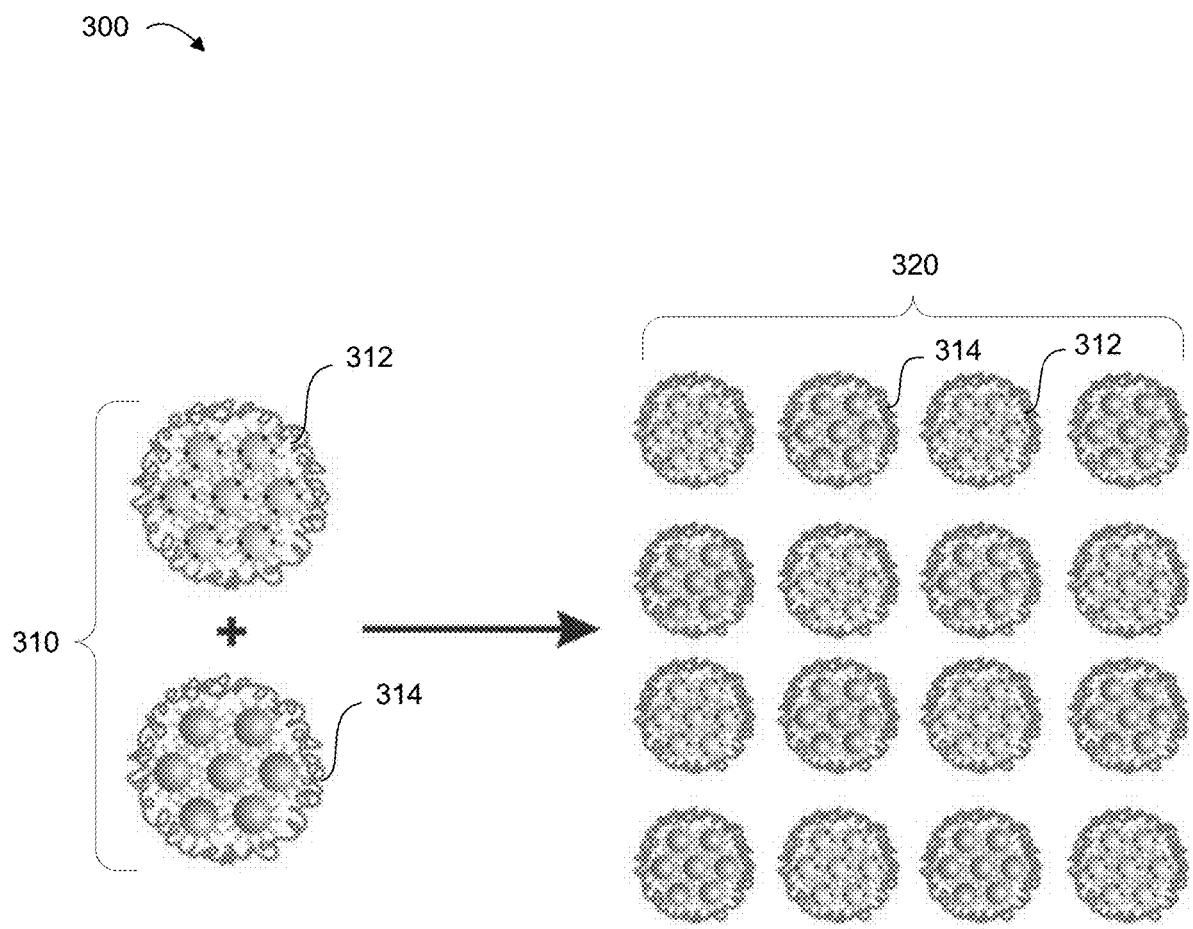
FIG. 1.3

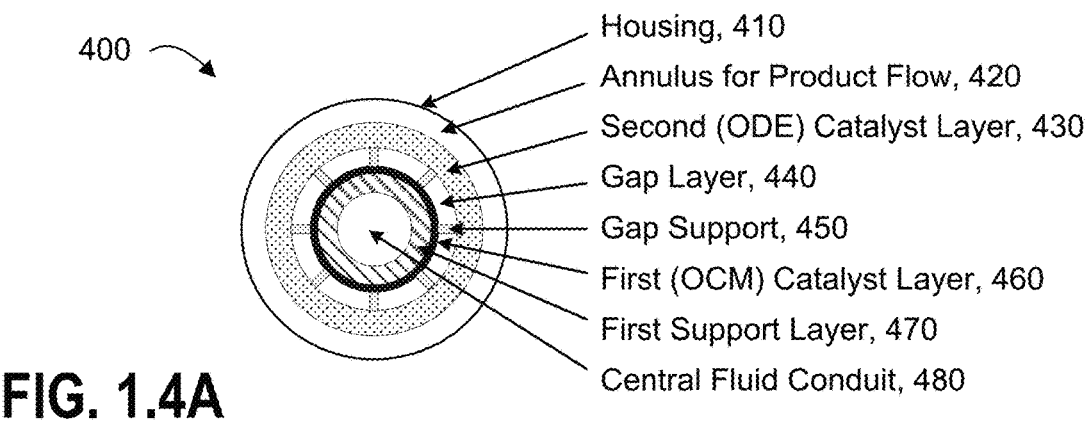
FIG. 1.4A
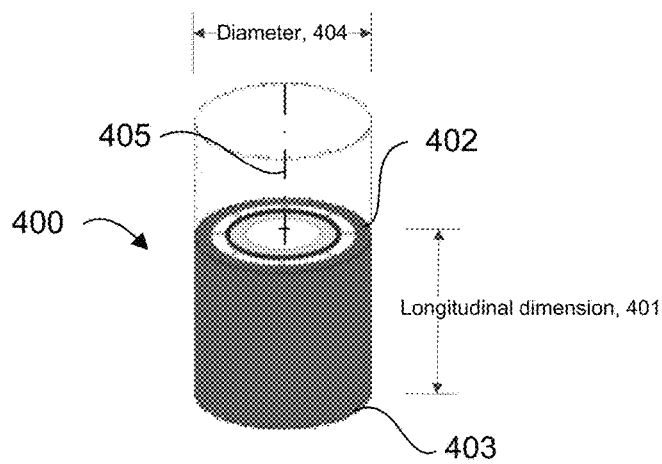
FIG. 1.4B
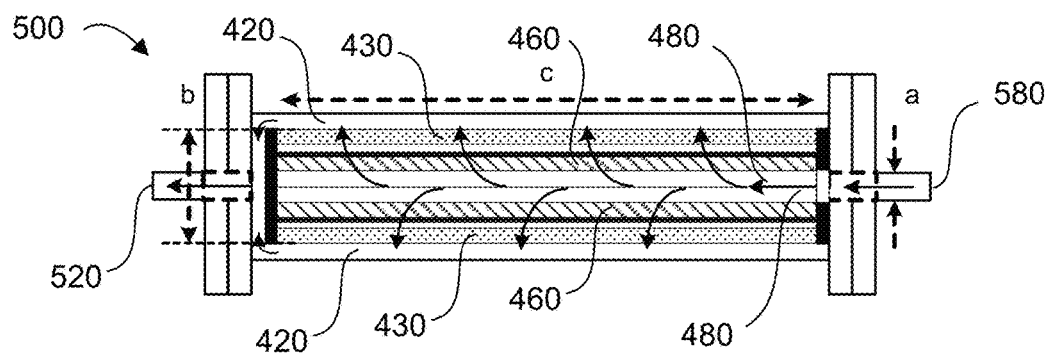
FIG. 1.4C

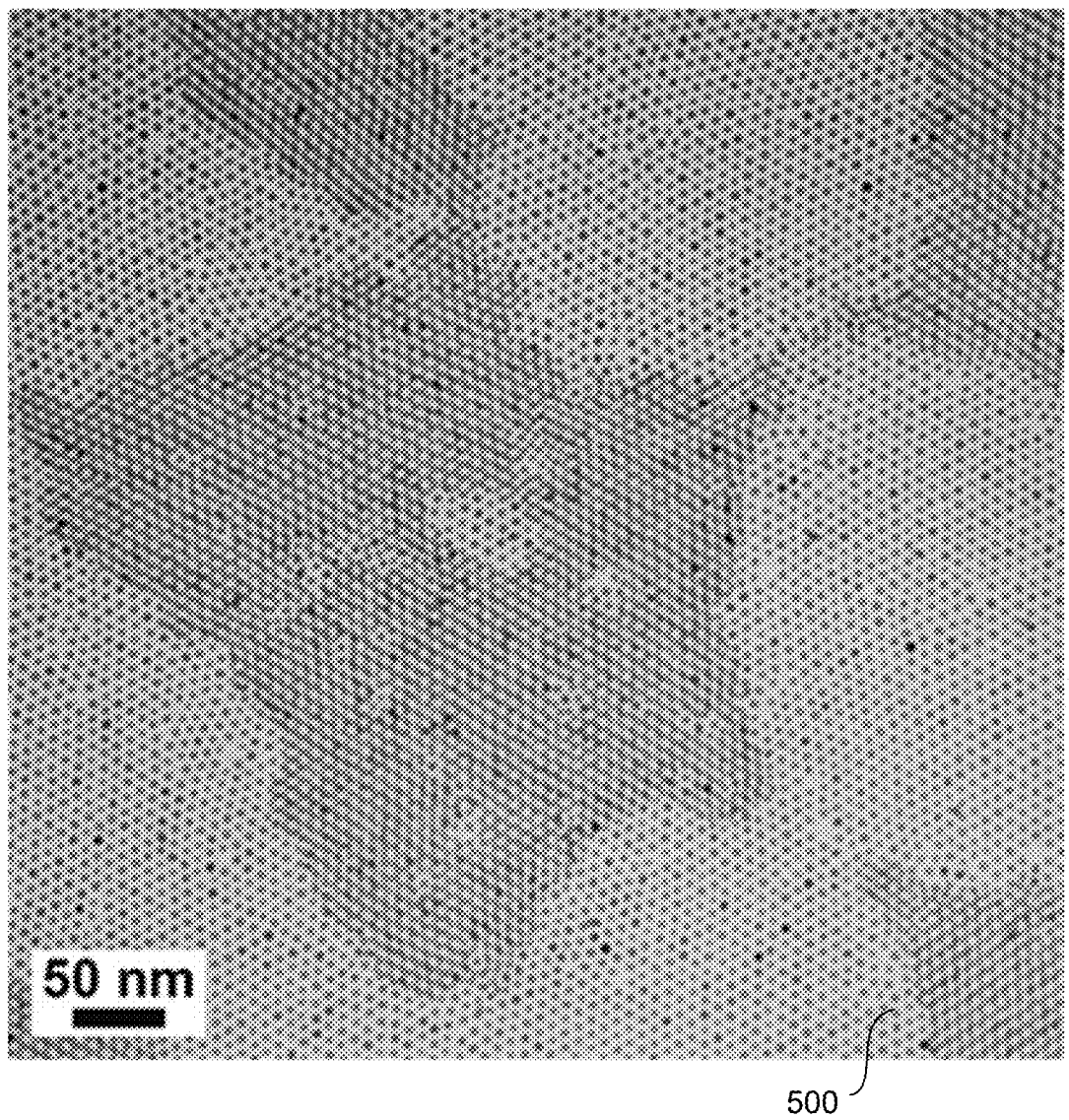
FIG. 1.5

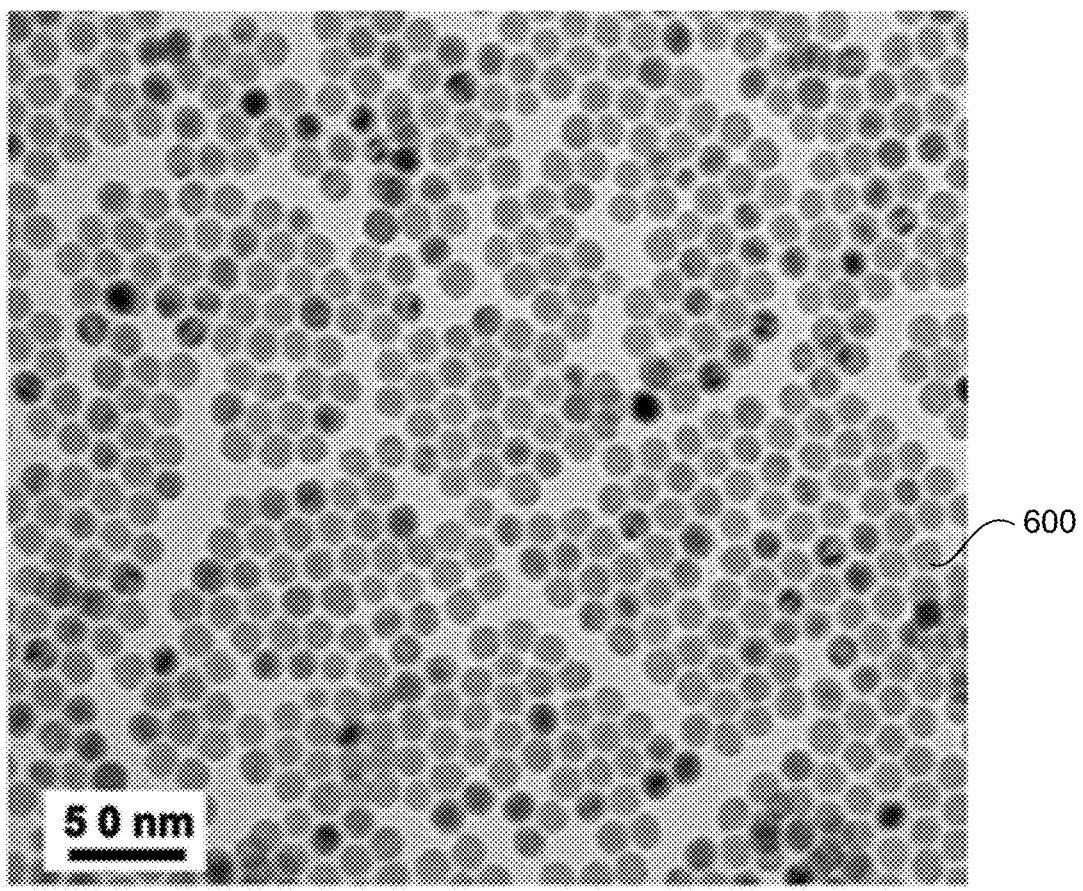
FIG. 1.6

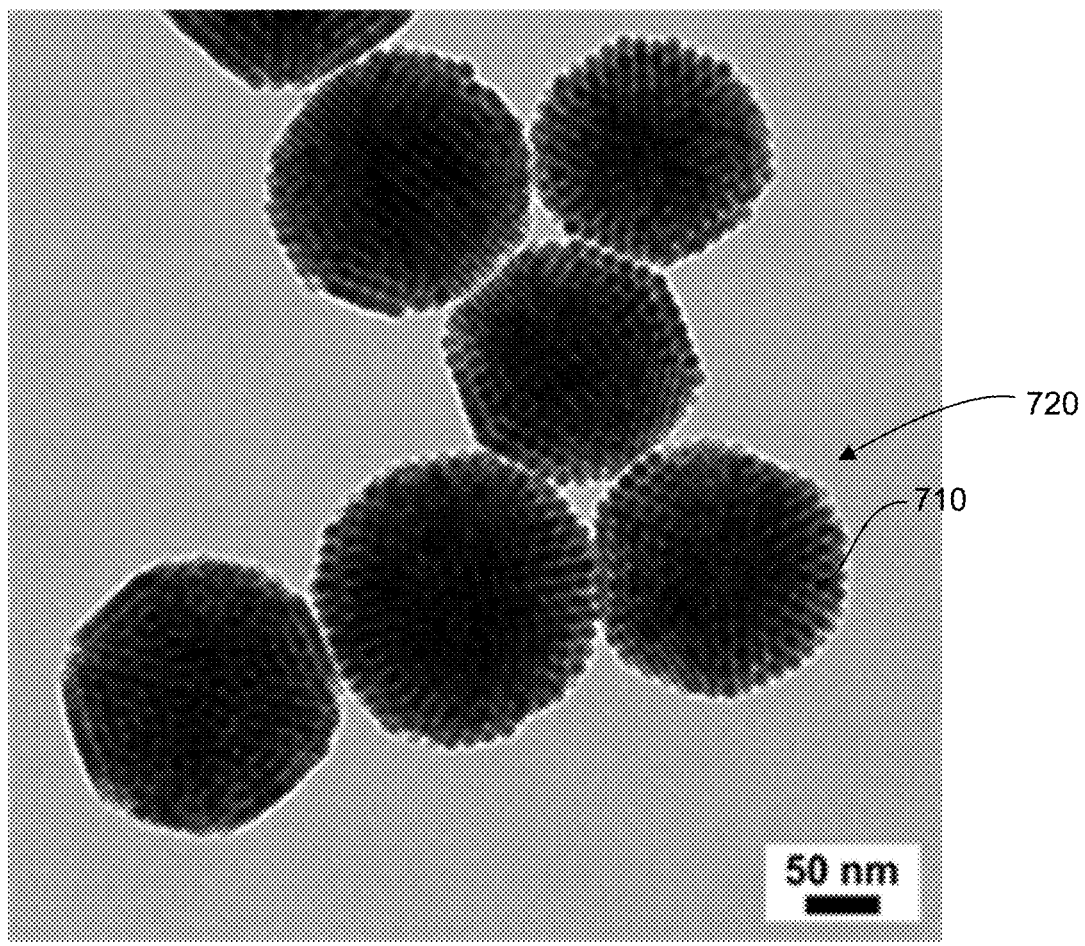
FIG. 1.7

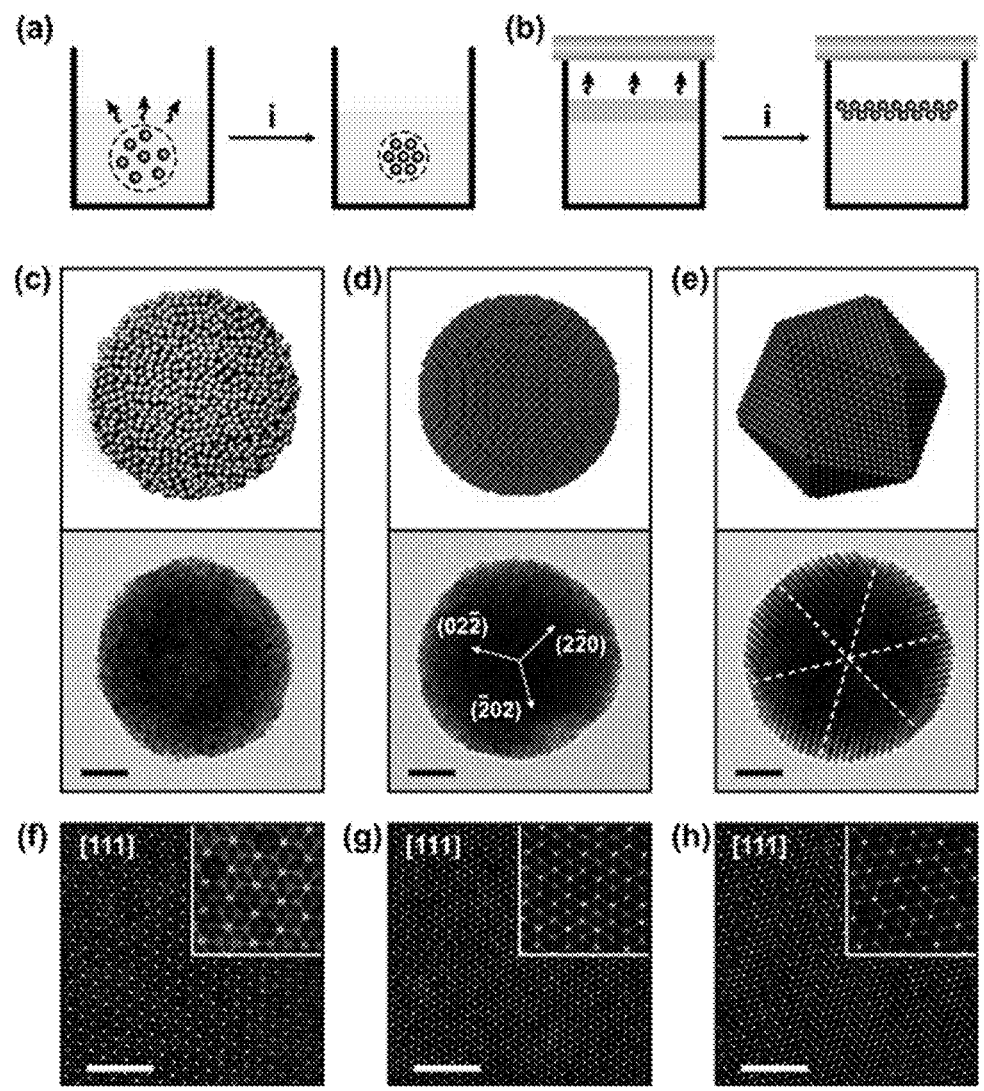
FIG. 2.1

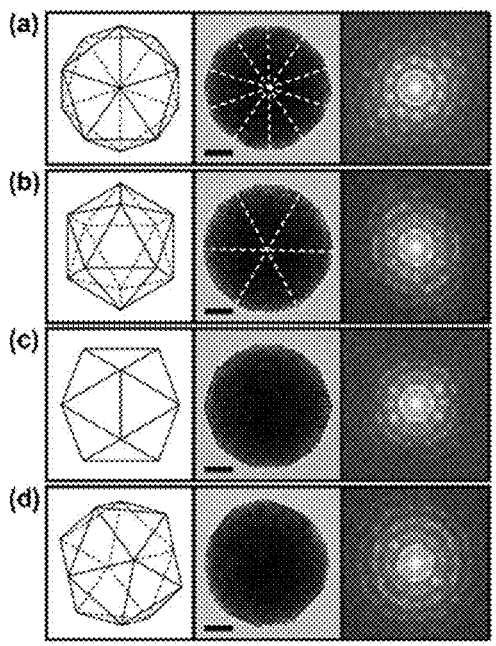
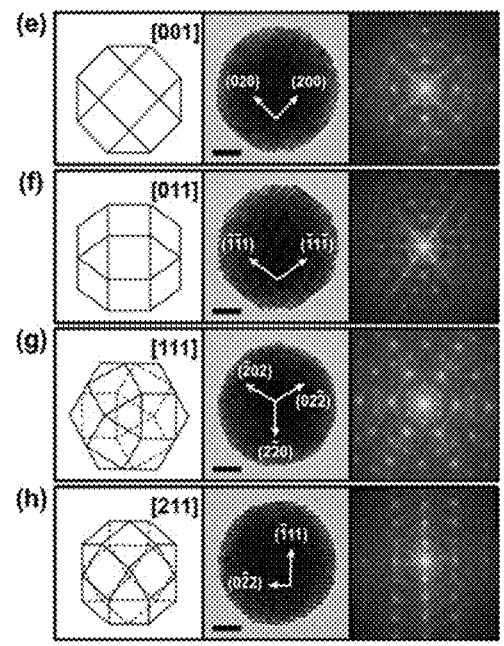
FIG. 2.2
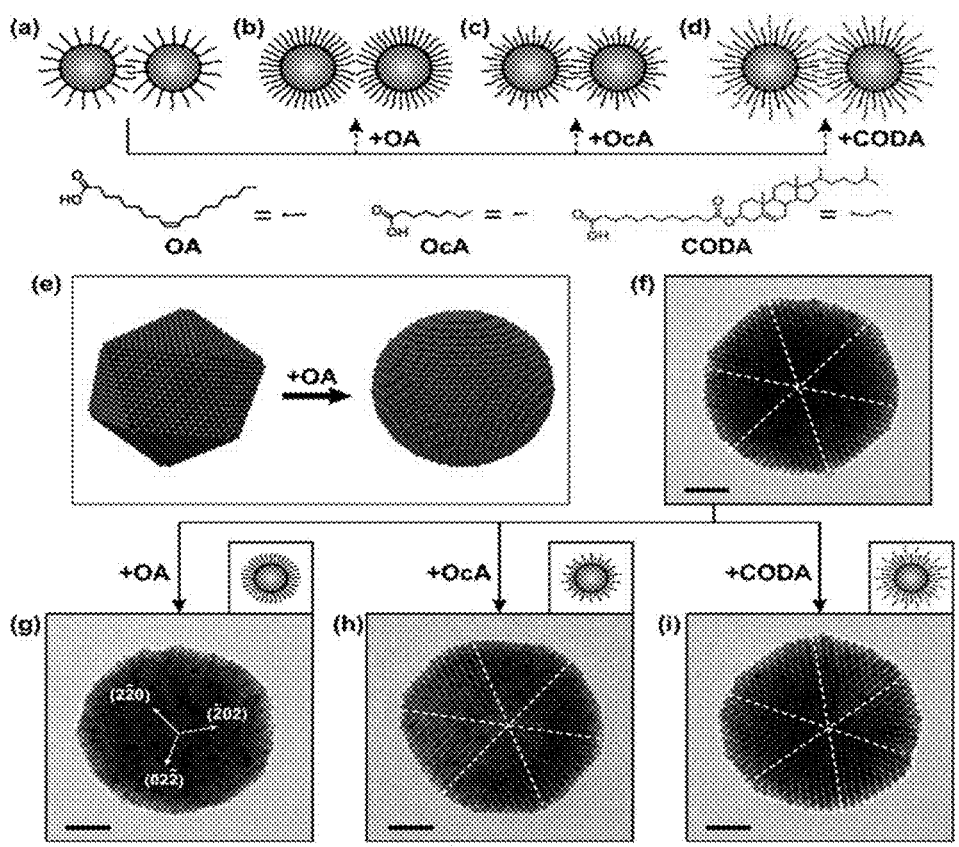
FIG. 2.3

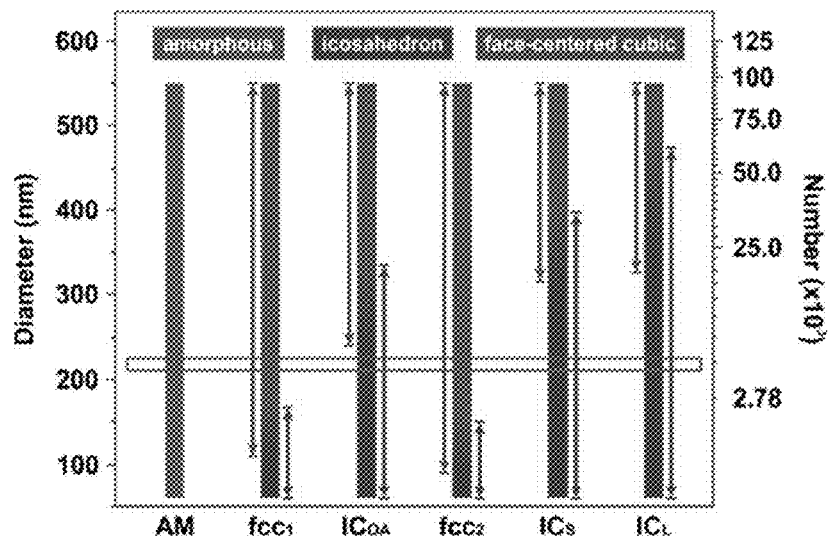
FIG. 2.4
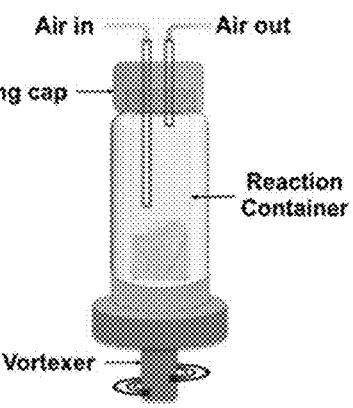
FIG. 2.5
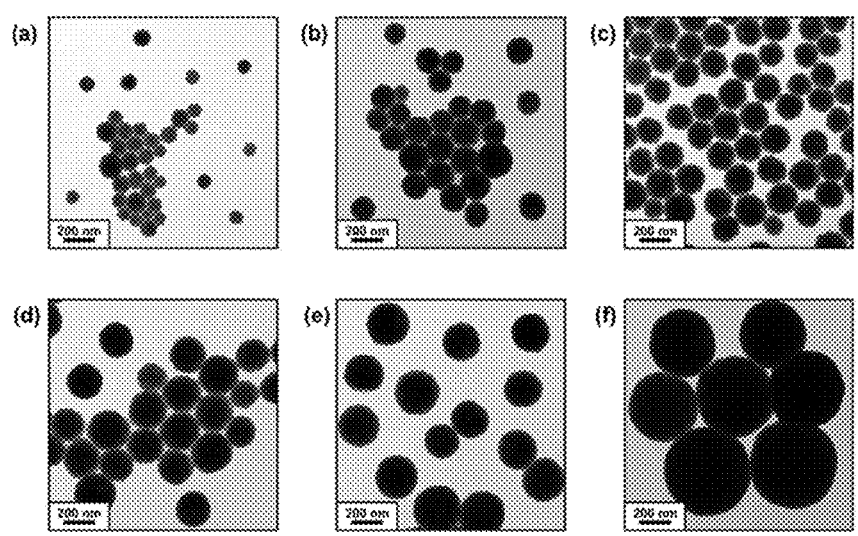
FIG. 2.6

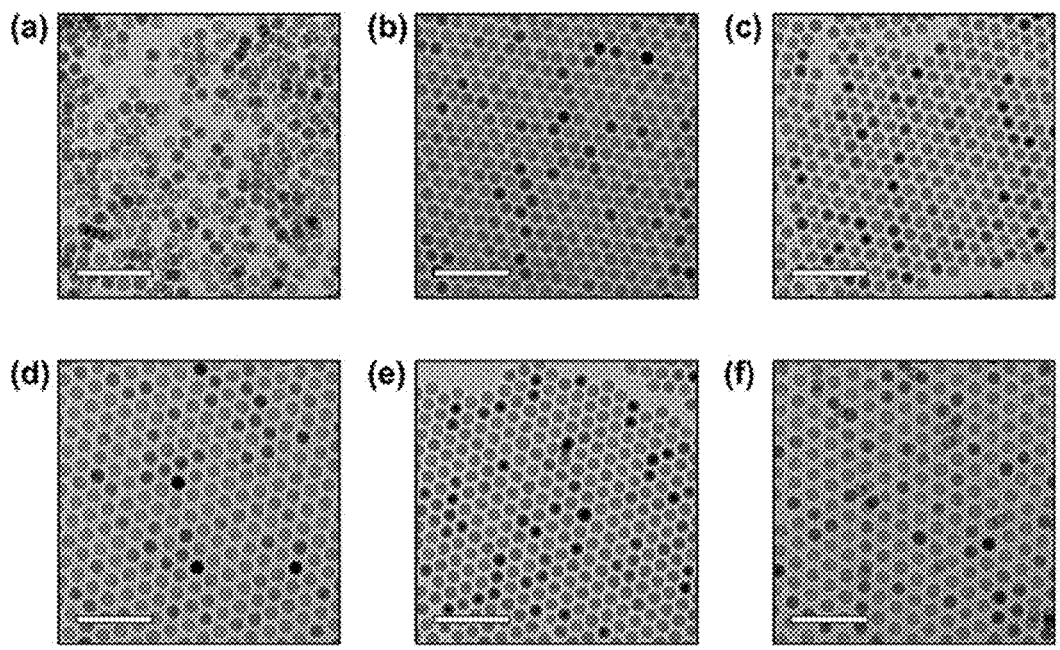
FIG. 2.7
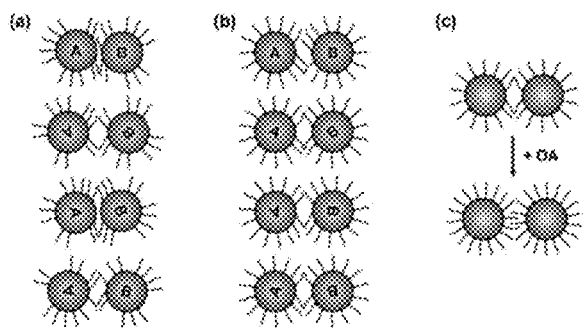
FIG. 2.8
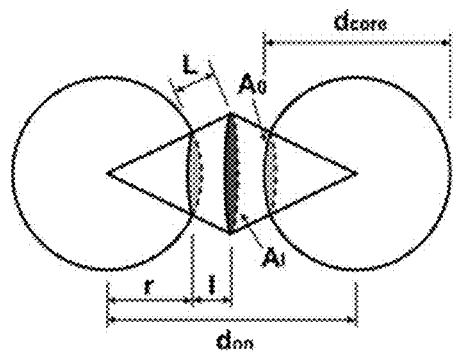
FIG. 2.9
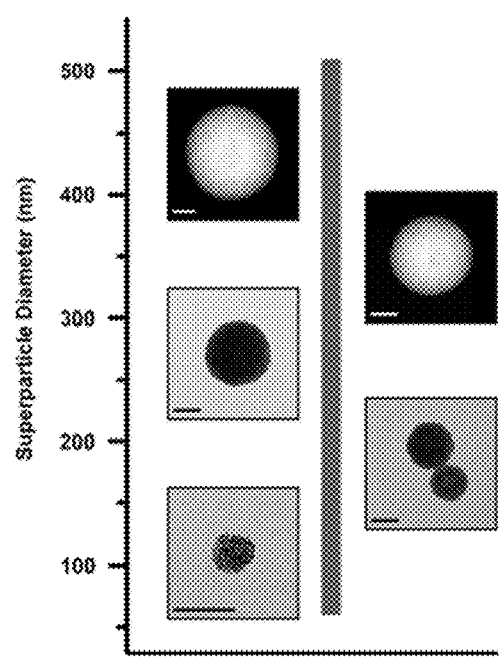
FIG. 2.10

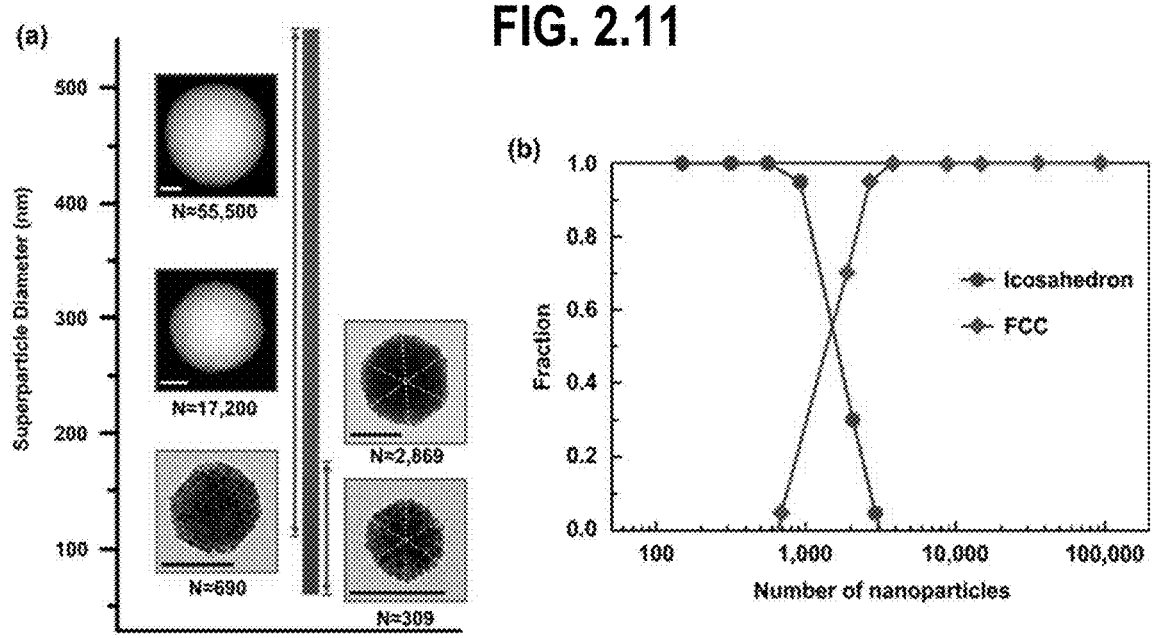
FIG. 2.11
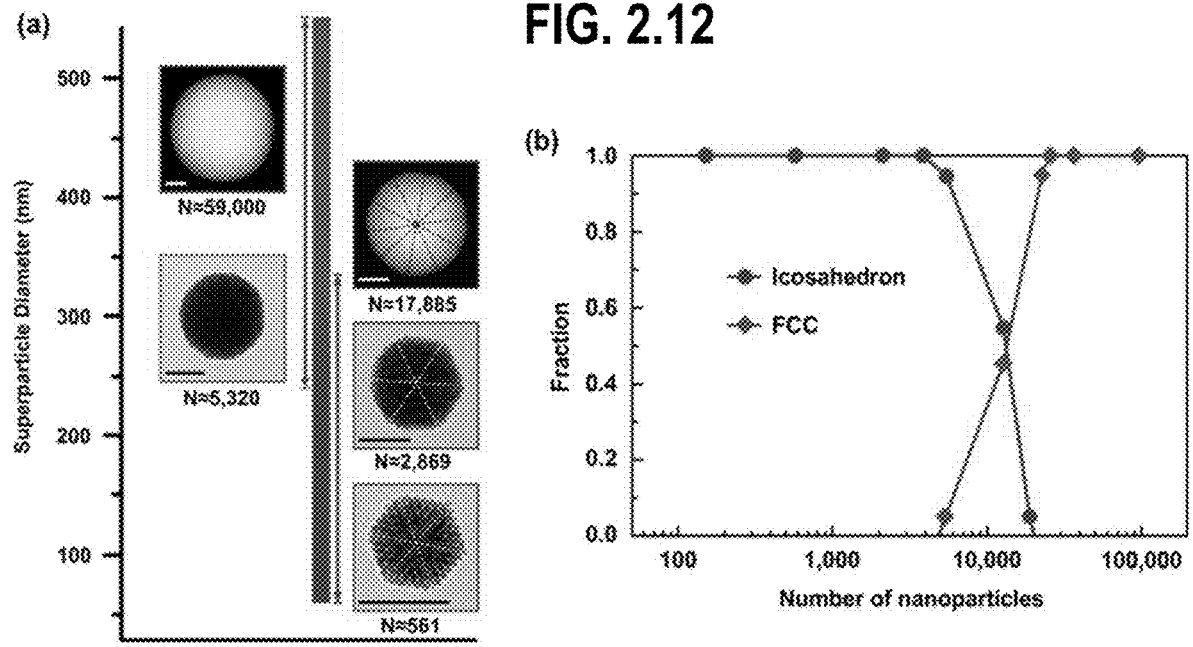
FIG. 2.12

FIG. 2.13
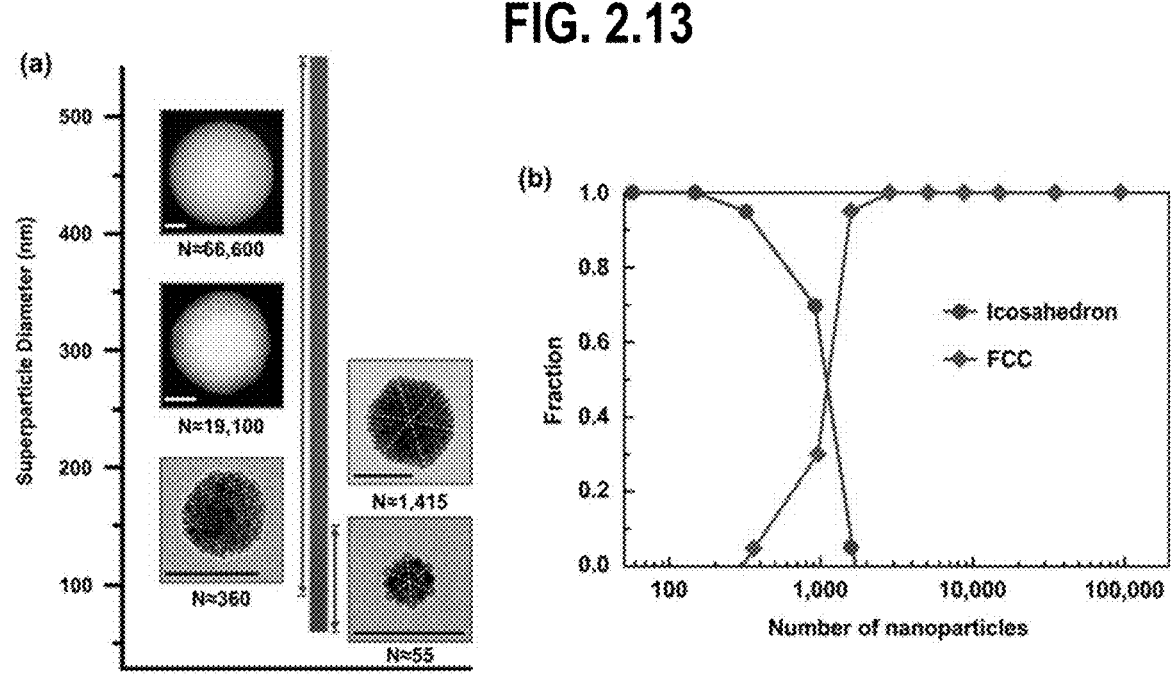
FIG. 2.14
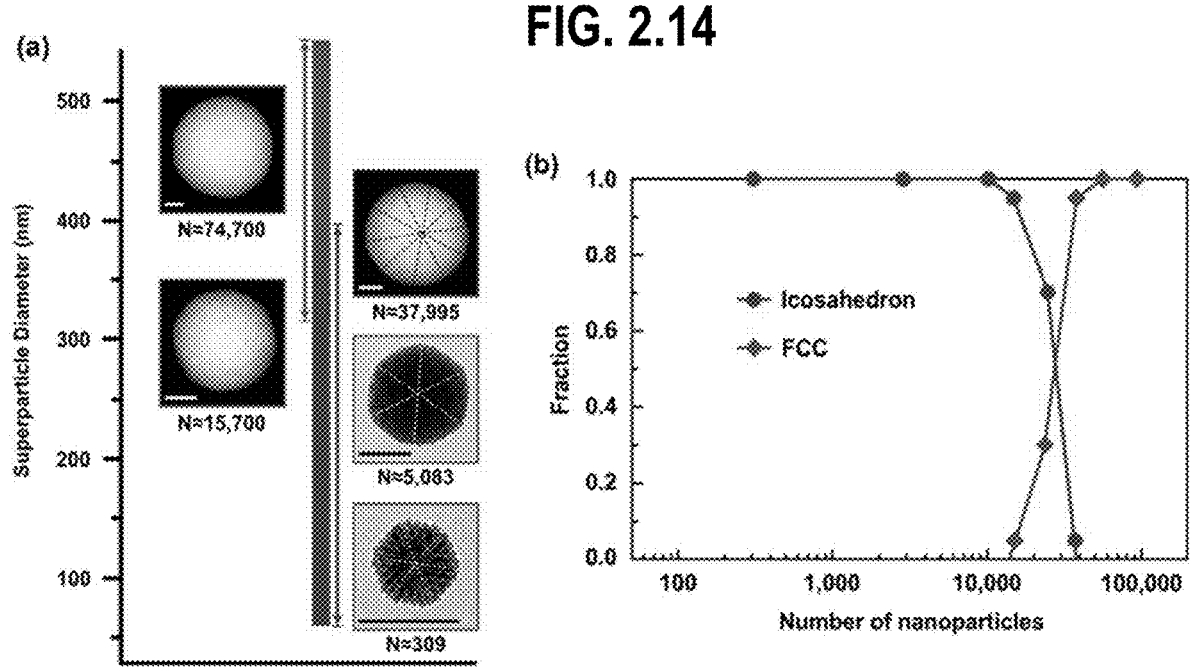

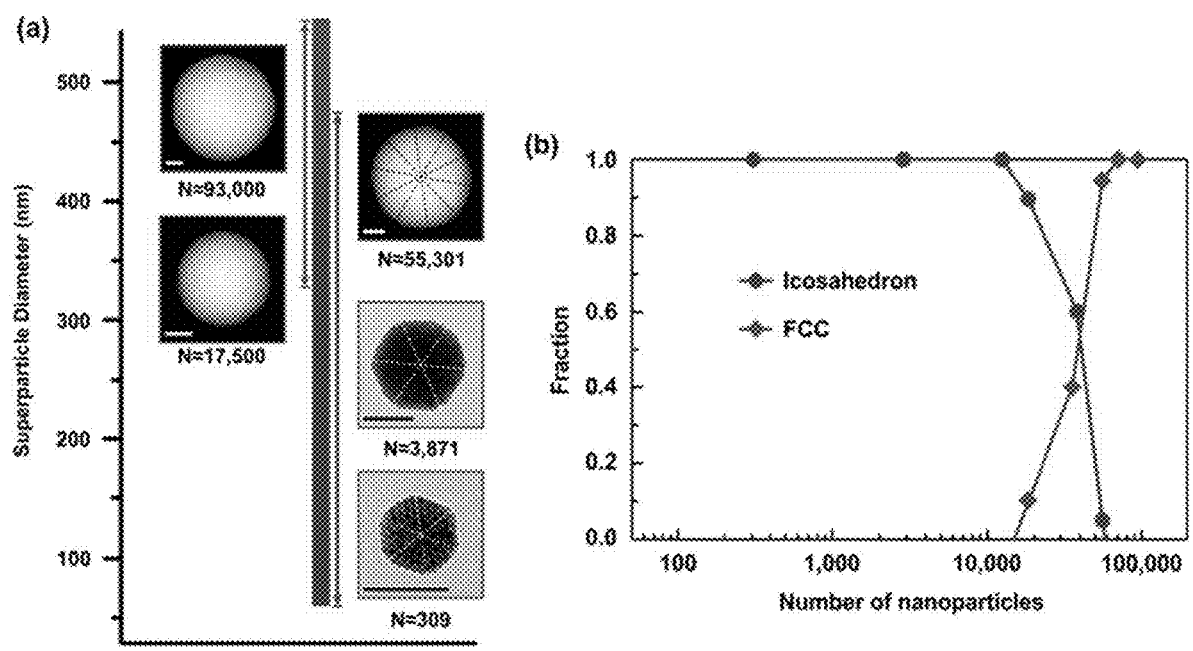
FIG. 2.15

SINGLE-ATOM-BASED CATALYST SYSTEMS

CROSS-REFERENCE TO RELATED APPLICATIONS

This application is a by-pass continuation application of the 35 U.S.C. § 371 national stage application of PCT Application entitled "SINGLE-ATOM-BASED CATALYST SYSTEMS" having international application number PCT/US2019/047233 filed Aug. 20, 2019, where the PCT claims priority to, and the benefit of the contents of U.S. provisional application having Ser. No. 62/719,848, filed on Aug. 20, 2018, which is incorporated herein by reference in its entirety.

BACKGROUND

Methane is the most abundant organic compound on earth, and it is the main constituent of natural gas (typically more than 90%). To date, a few large-scale commercial gas-to-liquid plants have been in operation (Ref. 1, Ex. 1) but they are based on an indirect route and complex Fischer-Tropsch technology with high capital costs. To be competitive, these plants rely on low cost natural gas and high crude oil prices (significantly higher than the current crude oil prices of approximately $40 per barrel).

Direct conversion of methane to higher value chemicals (e.g., ethylene) would be much more cost-effective. (Refs. 2, 3, Ex. 1) Ethylene is a major hydrocarbon building block in industry; (Ref. 4, Ex. 1) its worldwide production was over 150 million tonnes in 2016, which exceeds that of any other man-made organic compound. Currently, ethylene is produced from crude oil in a multistep high-temperature (~950° C.) process (Ref. 5, Ex. 1), and is the largest contributor to greenhouse gas emissions in the chemical industry. Therefore, the ability to use methane as the raw material in the production of ethylene, fuels and other higher value chemicals would be highly advantageous due to the abundance of low cost, domestic natural gas, (Ref. 6, Ex. 1) and the potential for using biogas in the future.

These needs and other needs are satisfied by the present disclosure.

SUMMARY

In accordance with the purpose(s) of the disclosure, as embodied and broadly described herein, the disclosure, in one aspect, relates to a single-atom-based catalyst system with single-atom catalytic sites in a controlled hierarchical structure over length scales ranging from macroscopic dimensions down to atomic scales, the single-atom-based catalyst system comprising: at least one catalyst structure comprising a first assembly of a plurality of single-atom-catalyst superparticles, further comprising a second assembly of a plurality of single-atom-catalyst nanoparticles.

According to one aspect, each of the single-atom-catalyst nanoparticles comprises a core-shell support structure having a crystalline metal oxide support surface, and one or more single-atom catalysts anchored to the support surface, wherein the density and location of the single-atom catalysts on the support surface are controlled within a 20% variance to provide a highly uniform spatial distribution of single-atom catalysts. Further, each of the second assemblies is a sub-micron-sized superlattice of a plurality of the single-atom-catalyst nanoparticles, the superlattice having a second density and a second porosity, wherein the second density is controlled within a 20% variance to provide a single-atom-catalyst superparticle having a precise porosity and a highly uniform spatial distribution of the single-atom catalysts. The first assembly of single atom-catalyst superparticles has a first density and a first porosity, wherein the first density of the first assembly is controlled within a 10% variance to provide a catalyst structure having a precise porosity and highly uniform spatial distribution of the single-atom catalysts. Optionally, the single-atom-based catalyst system can comprise one or more catalytically-inactive support materials.

According to some aspects, a tandem catalyst structure can comprise: a first catalyst layer comprising a first catalyst structure; and a second catalyst layer in fluid communication with the first catalyst layer, said second catalyst layer comprising a second catalyst structure. Optionally, the first catalyst layer, the second catalyst layer, or both can comprise a support layer comprising a catalytically inactive supporter material that supports the respective catalyst structure and/or a spacer layer.

According to additional aspects, a method for three-dimensional printing a single-atom-based catalyst system, such as those described herein, can comprise: providing a first ink substrate comprising a plurality of positively-charged first single-atom-catalyst superparticles; providing a second ink substrate comprising a plurality of positively-charged second single-atom-catalyst superparticles; providing a support ink substrate comprising a plurality of catalytically inactive supporter particles; providing a binder ink substrate comprising a plurality of negatively-charged polymeric binders; and selectively depositing with a 3D printing apparatus each of the first ink substrate, the second ink substrate, the support substrate, and the binder ink substrate to provide the elements of the single-atom-based catalyst system.

According to additional aspects, a method of converting methane to ethylene can comprise providing a single-atom-based catalyst system as described herein, wherein the single-atom-based catalyst system has a first catalyst layer comprising a first catalyst for the oxidative coupling of methane (OCM) into ethane and a second catalyst layer comprising a second catalyst for the oxidative dehydration of ethane (ODE) to ethylene; wherein the method comprises: introducing a first fluid comprising methane to the single-atom-based catalyst system; passing the first fluid through the first catalyst layer so that at least a portion of the methane contacts the first single-atom catalyst structure, providing a first reaction product comprising ethane; passing the first reaction product through the second catalyst layer so that at least a portion of the ethane contacts the second single-atom catalyst structure, providing a second reaction product comprising ethylene; and withdrawing the second reaction product from the single-atom-based catalyst system.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE FIGURES

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1.1 shows a schematic diagram illustrating an exemplary method of synthesizing single-atom-catalyst nanoparticles, including: step: core synthesis, step II: shell growth, step III: crystallization, and step IV: surface doping.

FIGS. 1.2A and 1.2B show schematic diagrams illustrating an exemplary method of synthesizing superparticles, including: step I(a,b) formation of nanoparticle micelles and step II(a,b): formation of superparticles. Different shades represent different materials/compositions.

FIG. 1.3 shows a schematic diagram illustrating an exemplary method of self-Assembly of superparticles into superstructures with controlled structural porosity with precision at the sub-micron scale.

FIGS. 1.4A-1.4C show a schematic diagrams illustrating an exemplary 3-D printed catalyst pellet as part of a reactor assembly. FIG. 1.4A shows a front elevation view of an exemplary catalyst pellet with a radial structure. FIG. 1.4B shows a perspective view of an exemplary catalyst pellet with a radial structure. FIG. 1.4C shows a partial side view of an exemplary catalyst pellet in a reactor assembly.

FIG. 1.5 shows a TEM image of exemplary 6.0-nm $Fe_3O_4$ Nanocrystals, in accordance with the Examples.

FIG. 1.6 shows TEM image of exemplary Sm-doped $Fe_3O_4$/MgO core/shell Nanocrystals, in accordance with the Examples.

FIG. 1.7 shows TEM image of exemplary superparticles showing exemplary assemblies of Sm-doped $Fe_3O_4$/MgO core/shell Nanocrystals, in accordance with the Examples.

FIG. 2.1 illustrates schematic of preparation process of superparticles in a closed system inside an emulsion droplet (a), and of superlattices in an open system at the liquid-air interface (b). c-e) 3D model (top) and TEM image (bottom) of a superparticle in amorphous (c), face-centered cubic (d), and icosahedral structure (e). f-h) Superlattices formed at the liquid-air interface using AM nanoparticles (f), $fcc_1$ nanoparticles (g), and $IC_{OA}$ nanoparticles (h). TEM images of nanoparticle superlattices in [111] projection (inserts, magnified view). Scale bars 50 nm.

FIG. 2.2 illustrates TEM images of an icosahedral superparticle in four characteristic orientations: "5-fold" orientation, with one 5-fold axis parallel to electron beam (a); "face" orientation, with one tetrahedral bounding face (111) resting on the substrate (b); "edge" orientation, with the common edge of two tetrahedra resting on the substrate and two 5-fold axes parallel to it (c); "parallel" orientation, with one corner resting on the substrate and one 5-fold axis parallel to it, the $IC_{OA}$ particle was tilted around 10° out of the "edge" toward the "5-fold" orientation (d); together with model (left) and FFT pattern (right). e-h) TEM images of two face-centered cubic superparticles in various orientations: images of the [001] and [011] zone directions are from one superparticle (e-f), and images of the [111] and [211] zone directions are from another superparticle (g-h), together with model (left) and FFT pattern (right). Scale bars 50 nm.

FIG. 2.3 illustrates a) schematics of proposed "effective bonding domain" formed via interdigitation of hydrocarbon chains of OA ligands between neighboring nanoparticles; b) hydrocarbon chain interdigitation is suppressed at a higher surface OA-ligand grafting density; c-d) schematics of proposed interparticle interaction configurations after loading OcA (c) and CODA (d), which increases ligand coverage but maintains the interdigitation of surface ligands. Ligand length was estimated as oleic acid: 2.04 nm; octanoic acid: 0.89 nm; and CODA: 3.48 nm. FIG. 2.3, in section e), illustrates a 3D model of proposed phase transition from an IC to an fcc superparticle by loading additional OA onto $IC_{OA}$ nanoparticles. FIG. 2.3, in section f), illustrates a TEM image of IC superparticle formed with $IC_{OA}$ nanoparticles; while g-i) TEM images of superparticles formed with three types of building block nanoparticles, which were prepared from $IC_{OA}$ nanoparticles via loading additional oleic acid (g), octanoic acid (h), and CODA (i). The corresponding schematic of interparticle interacting configurations are shown in (b), (c), and (d), respectively. Scale bars 50 nm.

FIG. 2.4 illustrates a phase diagram of superparticles synthesized from six types of nanoparticles with different surface-ligand configurations: fractions of identified structures as a function of superparticle diameter, and the corresponding building block numbers (n) labeled in the right y-axis with an $n^{1/3}$ plot. The amorphous, fcc and IC structure are labelled as gray, blue, and red, respectively. Blue and red double arrows indicate the diameter range for identified fcc and IC superparticles, respectively. Additional TEM or STEM images and phase diagrams containing detailed fraction numbers and superparticle sizes are available in the supporting information, FIGS. 2.10-2.15. AM, $fcc_1$, $IC_{OA}$, and $fcc_2$ represent nanoparticles with oleic acid coverage of 2.54, 2.87, 3.38, and 4.07 ligand·$nm^{-2}$, respectively; $IC_S$ represents nanoparticles covered with an oleic acid and octanoic acid mixture; $IC_L$ represents nanoparticles covered with an oleic acid and CODA mixture. Superparticles shown in FIGS. 2.1-2.3 have sizes located in the narrow green box.

FIG. 2.5 illustrates experimental setup for superparticle synthesis.

FIG. 2.6 illustrates TEM images of superparticles synthesized at different sizes: a) 91.3±18.2 nm, b) 162.7±17.4 nm, c) 183.5±20.6 nm, d) 233.6±24.2 nm, e) 285.4±25.6 nm, and f) 483.5±60.4 nm.

FIG. 2.7 illustrates TEM images of building block nanoparticle AM (a), $fcc_1$ (b), $IC_{OA}$ (c), $fcc_2$ (d), $IC_S$ (e), and $IC_L$ (f). (please see FIG. 2.4 in the main text for the meaning of these labels). Sample was prepared by directly dropping nanoparticle solution onto a TEM carbon grid. The interparticle distances between close-packed nanoparticles of each ligand density are 2.1±0.6 nm (a), 2.3±0.2 nm (b), 2.7±0.3 nm (c), 3.8±0.2 nm (d), 2.8±0.3 nm (e), and 4.8±0.3 nm (f). The diameter of $Fe_3O_4$ used for superparticle synthesis is 9.0±0.4 nm. Scale bars 50 nm.

FIG. 2.8 illustrates a schematic of proposed interparticle ligand interacting configurations of AM (a) and $fcc_1$ (b). For AM, the low ligand coverage could lead to uneven distribution of surface ligand, for which the interparticle distance varies depending on the orientation of ligand packing; therefore, amorphous superparticles were obtained. However, for $fcc_1$, with slightly higher ligand coverage, the ligand distribution is more uniform, but the ligand density is not high enough to form effective cooperative ligand interdigitation-"effective bonding domains"-resulting in weak interparticle interactions. Therefore, face-centered cubic superparticles were formed. c) Schematic of proposed interparticle interacting configuration change in $IC_{OA}$ particle pairs due to the increase of oleic acid coverage. An $fcc_1$ particle pair showed on the top and an $IC_{OA}$ particle pair shown at the bottom.

FIG. 2.9 illustrates a schematic of ligand interdigitation cone.

FIG. 2.10 illustrates TEM and STEM images of representative amorphous superparticles made from AM building block nanoparticles at different sizes. Scale bars 100 nm.

FIG. 2.11 illustrates TEM and STEM images of representative amorphous superparticles made from AM building block nanoparticles at different sizes. Scale bars 100 nm.

FIG. 2.12 illustrates, in section a), TEM and STEM images of representative superparticles formed with $IC_{OA}$ building block nanoparticles, taken from for from 215 superparticles. Number of building blocks labeled as N, scale bars 100 nm. FIG. 2.12, in section b), illustrates the percentage of superparticles observed at different sizes, plotted as a function of the number of nanoparticles per superparticle.

FIG. 2.13, in section a), illustrates TEM and STEM images of representative superparticles formed with $fcc_2$ building block nanoparticles, taken from 245 superparticles. Number of building blocks labeled as N, scale bars 100 nm. FIG. 2.13, in section b), illustrates the percentage of superparticles observed at different sizes, plotted as a function of the number of nanoparticles per superparticle.

FIG. 2.14, in section a), illustrates TEM and STEM images of representative superparticles formed with $IC_S$ building block nanoparticles, taken from 203 superparticles. Number of building blocks labeled as N, scale bars 100 nm. FIG. 2.14, in section (b), illustrates the percentage of superparticles observed at different sizes, plotted as a function of the number of nanoparticles per superparticle.

FIG. 2.15, in section (a), illustrates TEM and STEM images of representative superparticles formed with $IC_L$ building block nanoparticles, taken from 231 superparticles. Number of building blocks labeled as N, scale bars 100 nm. FIG. 2.15, in section (b), illustrates the percentage of superparticles observed at different sizes, plotted as a function of the number of nanoparticles per superparticle.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The disclosure pertains to a total-length-scale control approach to design and construction of heterogeneous catalysts, such as those to be used for direct conversion of natural gas to higher value chemicals. At the atomic scale, a single-atom catalyst nanoparticle can be synthesized with precise control over the location of the catalyst on the nanoparticle. Chemical-composition and lattice-strain engineering principals can be used to control the crystal structure of the nanoparticle and surface habits of catalyst matrices and to stabilize single-atom catalytic sites at high reaction temperatures, which also allows fine-tuning of the selectivity and activity of these single-atom sites. At the nanometer scale, a plurality of the nanoparticles can be assembled to form a sub-micron scale superparticle. For example, a nanoparticle self-assembly method can be used to control catalyst porosity and to increase the volume density of single-atom catalytic sites in sub-micrometer superparticles. At the macroscopic scale, the superparticles may be assembled into composite catalyst structures. For example, a 3-D printing technique can be employed to assemble the superparticles into composite catalyst pellets with sub-millimeter scale structures, allowing fine control over reaction kinetics to minimize non-selectively oxidization of methane and to maximize the ethylene production yield.

This total-length-scale control approach is comprehensive for design of functional materials. It can be readily extended for construct the powerful single-atom catalysts for other reactions with extraordinarily high selectivity and activity, as well as reaction kinetics control ability. This may open an opportunity to modernize many of conventional catalysts with improved chemoselectivity, allowing the production of daily used chemicals (e.g., food packaging materials, eyeglasses, medical devices, display liquid crystals, lubricants and engine coolants) in a cheaper, greener and energy more efficient manner.

In addition, the disclosed methods and devices potentially make the direct conversion of methane to ethylene economically viable for industrial operation. This can have a significant economic impact, since abundant domestic natural gas can be utilized rather than foreign oil, and this synthesis route have a higher overall energy efficiency and lower greenhouse-gas emission as compared to current ethylene production route using petroleum-based naphtha.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, materials science, mechanical engineering, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by volume, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequences where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

In accordance with the purpose(s) of the present disclosure, as embodied and broadly described herein, embodiments of the present disclosure relate to single-atom-catalyst systems having total-length-scale control of single-atom catalytic sites. In other words, the single-atom-catalyst systems have single-atom catalytic sites in a controlled hierarchical structure over entire length scales ranging from macroscopic dimensions down to atomic scales. The various embodiments disclosed herein provide a method of using a lattice strain in core-shell nanoparticles to stabilize single-atom catalytic sites on their surface. The existence of lattice strain could also affect the selectivity and reactivity of these catalytic sites. The various embodiments also provide a method of using most closely packed supercrystalline superparticles to increase the volume loading density of single-atom catalytic sites, which could, in principle, be more than 10 times higher than that of the current single-atom catalysts reported in literature. Further embodiments relate to a method that employs a 3D printing technique to construct macroscopic catalyst pellets, which can further optimize the proposed tandem catalysts from a materials engineering standpoint, and potentially making direct conversion of methane to ethylene economically viable for industry.

According to the various embodiments, the single-atom-based catalyst system comprises a catalyst structure comprising a first assembly of a plurality of single-atom-catalyst superparticles, further comprising a second assembly of a plurality of single-atom-catalyst nanoparticles, described further herein.

A. ATOMIC SCALE

According to some embodiments, preparation of the single-atom-catalyst system can start at the atomic scale. At this level, chemical-composition and lattice-strain engineering can be used to assemble nanoparticles to provide a core-shell support structure having a controlled crystalline support surface. One or more single-atom-based active catalysts can be doped onto the support surface in a highly controlled manner to provide a nanostructure having a highly uniform distribution of single-atom catalyst sites.

In one aspect, providing single-atom-catalyst nanoparticles comprises synthesizing core-shell nanoparticles having position-controlled dopants comprising the catalytic active material. Exemplary methods and materials for forming the nanoparticles include, but are not limited to, those described in U.S. Pat. No. 9,406,759 to Cao, the disclosure of which is incorporated herein by reference, to the extent consistent with the present disclosure. According to the embodiments, the step of providing a single-atom-catalyst nanoparticle comprises synthesizing a metal oxide core-shell structure. Referring to FIG. 1.1, an exemplary method 100 of forming a single-atom-catalyst nanoparticle includes a first step (step I) that includes selecting a core material 112 and synthesizing a core structure 110. According to various embodiments, the core material 112 is selected to provide a desirable lattice structure, and desirable chemical affinity for the shell material 122. In certain embodiments, the core material 112 comprises a metal oxide nanoparticle such as nickel oxide ($NiO_x$) or iron oxide ($FeO_x$), which have lattice constants that can be tuned to a predetermined value such as by controlling redox reactions through Kirkendall process. In embodiments, the core material 112 comprises a plurality of spherical nanoparticles having size (diameter) of about 10, or about 20, or about 30 nm (e.g., about 10 to 40 nm, about 10 to 30 nm, about 20 to 30 nm, about 10 to 20 nm, about 8 to 12 nm, about 18 to 22 nm, or about 28 to 32 nm). In embodiments, the size distribution of the nanoparticles in the core is within about 10% or within about 5% of a target size value.

According to various embodiments, the disclosed method 100 of providing a single-atom-catalyst nanoparticle further comprises a second step (step II) which includes selecting a shell material 122 and growing a shell 120 on the core structure 110. According to the various embodiments, the shell material 122 is selected to provide, for example, a suitable support structure for the nanoparticle, a desired chemical affinity to the core material 112, and a desired lattice matching to the core material 112. In certain embodiments, the shell material 122 comprises a metal oxide such as magnesium oxide (MgO), calcium oxide (CaO), silicon dioxide ($SiO_2$), nickel oxide ($NiO_x$), aluminum oxide ($AlO_x$), zinc oxide (ZnO), titanium oxide ($TiO_x$), or Graphene, or a combination thereof. In certain embodiments, the core material comprises $NiO_x$, and the shell material comprises MgO, CaO, or a combination thereof. In certain embodiments, the core material comprises $FeO_x$, and the shell material comprises $SiO_2$.

In an embodiment, the shell structures 120 can be introduced and grown on the cores using a solvent such as octadecene solution containing the respective organometallic precursors. For example, according to some embodiments, the shells 120 are grown on the core structure 110 to provide a shell thickness of from about 3 nm to about 8 nm. According to the various embodiments, the disclosed method 100 can include a further step (step III) which includes crystallizing the shell structure 120 to provide a crystallized shell structure 130 having a desired crystalline form. In an embodiment, the shell structure 120 can be annealed in a pure octadecene solution at 320 degrees C. to achieve a desired crystalline form. In some embodiments, the shell material 122 is MgO or CaO, and the resulting crystalline shell structure 130 is a cubic rocksalt structure. In some embodiments, the shell material 122 is $SiO_2$, and the resulting crystalline shell structure 130 is a tetragonal α-crystobalite crystal structure.

According to the embodiments, the disclosed method 100 of providing a single-atom-catalyst nanoparticle includes a further step (step IV) which includes position-controlled surface doping of the shell structure 130 with one or more single-atom-based catalytic active materials 142, forming the single-atom-catalyst nanoparticle 150. According to embodiments, a catalytic active material is selected, at least in part, for its desired catalytic activity. In various embodiments, at least one of the catalytic active materials is selected from samarium (Sm), iron (Fe), manganese (Mn), sodium (Na), tungsten (W), platinum (Pt), tin (Sn), nickel (Ni) or a combination thereof. In an embodiment, at least one of the single-atom-catalysts will be used as a catalyst for oxidative coupling of methane (OCM) into ethane, and the catalytic active material is Sm, Fe, Mn, Na, W, or a combination thereof. In an embodiment, at least one of the single-atom-catalysts will be used as a catalyst for oxidative dehydration of ethane (ODE) into ethylene, and the catalytic active material is Ni, Pt, Sn, or a combination thereof.

According to the various embodiments, the precursors of these one or more catalytic active materials are provided in an organometallic form with bulky ligands. The bulky ligands are selected to induce entropy effects to control the location of the dopants, e.g., to prevent growth of two dopants at neighboring lattice sites of the shell. Exemplary bulk ligands include ethyl-hexyl or heptyl-undecyl groups, or the like. In some embodiments, the number of dopants on a nanoparticle can be controlled, at least in part, by controlling the amount of the precursor of the catalytic active materials introduced to the nanoparticle.

According to some embodiments, the nanoparticles may comprise one or more types of single-atom catalysts. For example, in one embodiment, a single-atom-catalyst nanoparticle comprises a homo system of catalysts, for example only OCM catalysts or only ODE catalysts. In another embodiment, a single-atom-catalyst nanoparticle comprises a heterosystem of catalysts, for example having a combination of OCM catalysts, and ODE catalysts.

According to the embodiments, the resulting surface-doped nanoparticles can be activated to form single-atom catalysts. For example, the doped nanoparticles can be subject to stepwise pyrolysis of organic binding materials in the presence of oxygen at a temperature of about 600 degrees C. to about 1000 degrees C. The pyrolysis may be conducted for a period of time to produce a necessary or desired activation. In some embodiments, the pyrolysis may be performed for a period of from about three to about six hours.

In embodiments, the density and location of the single-atom-catalytic sites on the support surface are closely-controlled, e.g., within about a 20% variance, or within about 15% variance, or within about 10% variance, or within about 5% variance from a target value. Controlling the variance of the density and location of the single-atom-catalyst sites results in a single-atom-catalyst nanoparticle having a highly uniform spatial distribution of single-atom catalysts.

B. NANOSCALE

According to some aspects, preparation of the single-atom-catalyst system can continue at the nanometer scale. At this level, a plurality of the single-atom-catalyst nanoparticles described herein are further assembled into sub-micron-sized superlattices. The volume and density of the assembly of nanoparticles within the superlattice assembly can be precisely controlled so that the superlattice has a necessary or desired porosity. In addition the size, structure and configuration of the assembly of nanoparticles can be precisely controlled so that the resulting superparticle has a necessary or desired volume, density, and/or distribution of single-atom-based active catalyst sites.

According to some embodiments, a plurality of single-atom-catalyst nanoparticles (having a particle size of less than about 100 nm) can be assembled into superparticles having a micron or sub-micron size (e.g., about 0.02 to about 1 micron in diameter). As used herein, "superparticles" refers to nanoparticle assemblies (also referred to herein as "second assemblies") in the form of colloidal particles. The plurality of nanoparticles are bound together through non-covalent interactions. In some embodiments, the superparticles may be supercrystalline collections of nanoparticles, in other words, a plurality of nanoparticles arranged in a superlattice structure. According to the embodiments, the superparticles comprise an assembly of single-atom-catalyst nanoparticles that can be arranged to provide a predetermined reactivity. The reactivity of a superparticle can be controlled, at least in part, by controlling the volume loading density of single-atom catalytic sites, and the porosity of the superparticle structure. For example, nanoparticles assembled into close-packed superlattices can increase the volume loading density of single-atom-catalytic sites in a structure with controlled porosity. According to the various embodiments, the resulting superparticles can form stable colloids, which can be used as building blocks for constructing the radially-structured tandem catalysts described herein. Exemplary methods and materials for forming superparticles include those described in U.S. Patent Publication No. 2011/0150938 to Cao, et al, the disclosure of which is incorporated herein by reference, to the extent consistent with the present disclosure.

Referring to FIG. 1.2A, according to various embodiments, a method 200 of assembling the single-atom-catalyst superparticles comprises a first step (step Ia) of passivating the single-atom-catalyst nanoparticles 150 with hydrophobic ligands 212 to form an aqueous solution of nanoparticle micelles 210. The nanoparticles 150 can be passivated with a passivation agent such as dodecyl trimethylammonium bromide (DTAB). In a second step (step IIa), the solution comprising the nanoparticle-micelles 210 may then be mixed with a solvent to form a solution of colloidal superparticles 220*a*. In some embodiments, the solvent is a polar organic solvent (e.g., ethylene glycol, di-ethylene glycol, tri-ethylene glycol, diethanolamine, triethanolamine) an oxygen-containing organic solvent, or a combination thereof. The combination of the nanoparticle-micelle solution with the solvent can cause a controlled decomposition of the micelle structures, and controlled aggregation of the nanoparticles to form the superparticles. According to various embodiments, the size of the superparticles may be controlled, at least in part, by the amount of the passivation agent. According to certain embodiments, the resultant superparticles have a passively-charged surface and a size of about 250 nm.

According to some embodiments, the superparticles may comprise an assembly of one or more types of nanoparticles. For example, referring to FIG. 1.2A, in one embodiment, a single-atom-catalyst superparticle 220a comprises an assembly of a homo system of nanoparticles 150, for example only nanoparticles having OCM catalysts or only nanoparticles having ODE catalysts. Referring to FIG. 1.2B, in another embodiment, a single-atom-catalyst superparticle 220b comprises an assembly of a heterosystem of nanoparticles, for example having a combination of nanoparticles 150a having OCM catalysts 142a, and nanoparticles 150b having ODE catalysts 142b.

In embodiments, the density of the single-atom-catalyst nanoparticles within the superparticles can be closely-controlled, for example, within about a 20% variance, or within about 15% variance, or within about 10% variance, or within about 5% variance of a target value. Precise control of the density of the nanoparticles can provide a single-atom-catalyst superparticle having a precise porosity and a highly uniform spatial distribution of the single-atom catalysts.

C. MACROSCOPIC SCALE

According to some aspects, preparation of the single-atom-catalyst system can continue at the macroscopic scale. At this level, a plurality of the single-atom-catalyst superparticles described herein are further assembled into composite catalyst structures. The volume and density of the assembly of nanoparticles (also referred to herein as a "first assembly") can be precisely controlled so that the catalyst structure has a necessary or desired porosity, e.g., to provide a certain fluid throughput. In addition the size, structure and configuration of assembly of superparticles that make up the catalyst structure can be precisely controlled so that the resulting catalyst structure has a necessary or desired volume, density, and/or distribution of single-atom-based active catalyst sites. For example, in some embodiments, the density of the single-atom-catalyst superparticles within the single-atom-catalyst structure can be closely-controlled, e.g., within about a 10% variance, or within about 5% variance from a target value. Controlling the density and spatial distribution of the single-atom-based active catalyst sites can enable fine control over reaction kinetics, e.g., to optimize desired reactions and to minimize side reactions.

According to some embodiments, the single-atom-catalyst systems and/or structures may comprise one or more types of superparticles. For example, in one embodiment, a single-atom-catalyst system or structure comprises an assembly of a homo system of single-atom-catalyst superparticles, for example where all of the superparticles are substantially the same. In another embodiment, a single-atom-catalyst system or structure comprises an assembly of a heterosystem of superparticles, having superparticles with differing properties and/or structures and/or single-atom-catalyst species.

According to some aspects of the present disclosure, a method for making a single-atom-catalyst system, as described herein, comprises, generally, three-dimensional (3D) printing of one or more catalyst structures using one or more inks comprising a plurality of the single-atom-catalyst superparticles to form a predetermined assembly of the single-atom-catalyst superparticles. Generally speaking, 3D printing can be used to produce complex 3D objects directly from computer-aided digital design. 3D printing technologies include, among others: (1) stereolithography ("SLA"), (2) melt deposition modelling, or fused deposition modelling ("FDM"), (3) powder bed technology involving a laser beam and/or an E-beam, (4) multi jet fusion ("MJF"). SLA selectively solidifies photosensitive (UV curable) polymers by laser (e.g., laser sintering) or other light source, while FDM selectively deposits thermoplastic molten polymer through a heated nozzle. During MJF, an entire layer or several layers of a build material (also referred to as build material particles) is/are exposed to radiation, but a selected region (in some instances less than the entire layer(s)) of the build material is fused and hardened to become a layer or several layers of a 3D object/part. These or other techniques can be employed with the systems described herein.

Referring to FIG. 1.3, according to the embodiments, a method 300 of 3D printing the single-atom-catalyst system comprises depositing an ink 310 comprising one or more catalytically-active single-atom-catalyst superparticles (312, 314) to provide an assembly 320 of single-atom-catalyst superparticles (and, optionally, other components such as binders and catalytically-inactive particles) having a predetermined structure. According to the embodiments, an ink substrate 310 comprising the single-atom-catalyst superparticles can comprise a dispersion of the catalytically-active superparticles which are in the form of stable colloids in a dispersion media, such as an aqueous media. In some aspects, these catalytically-active superparticles can be functionalized with a plurality of surface ligands which stabilize the superparticles in the ink formulation. In some embodiments, the surface ligands can be either positively-charged or negatively-charged.

According to the embodiments, 3D printing the single-atom-catalyst system and/or structure further comprises depositing one or more catalytically-inactive particles, for example, those which can provide structural support for the assembly of catalytically-active superparticles. The catalytically-inactive particles can be provided as part of the ink substrate comprising the single-atom-catalyst superparticles, or can be provided as a separate ink composition. In some embodiments, the catalytically-inactive particles are provided in the form of stable colloids in a dispersion media, such as an aqueous media. These catalytically inactive particles are functionalized with a plurality of surface ligands which stabilize the superparticles in the ink formulation. In some embodiments, the surface ligands can be either positively charged or negatively charged.

According to the embodiments, 3D printing the single-atom-catalyst system further comprises depositing one or more binder inks to increase the structural stability of the catalyst system or structures (including assemblies of single-atom-catalyst superparticles and/or catalytically-inactive particles) during 3D printing. Exemplary binder inks comprise adhesive polymer substrates having a charge that is opposite to the charge of the catalytically-active superparticles and/or catalytically-inactive particles with which the binder is intended to interact. In other words, when the binder is intended to interact with catalytically-active superparticles or catalytically-inactive particles that are positively charged, the binder ink should be negatively charged, and vice versa.

According to the embodiments, the single-atom-catalyst system can comprise two or more single-atom catalyst structures, each structure comprising an assembly of respective single-atom-catalyst superparticles. For example, a single-atom-catalyst system can comprise a first region or first layer having a first single-atom-catalyst structure, and a second region or second layer comprising a second singleatom-catalyst structure. In some embodiments, the first single-atom-catalyst structure and the second single-atom-catalyst structure have the same active catalytic species. In some embodiments, the first single-atom-catalyst structure and the second single-atom-catalyst structure may have different active catalytic species. Structures comprising multiple active single-atom-catalyst species can be useful, for example, for multistep reactions. These single-atom catalyst systems can comprise one or more additional layers or structures, as necessary or desired, such as to provide support or spacing to the single-atom-catalyst system.

According to some embodiments, a method for making a single-atom-catalyst system comprises providing a first ink substrate comprising a plurality of positively-charged first single-atom-catalyst superparticles; providing a second ink substrate comprising a plurality of positively-charged second single-atom catalyst superparticles; providing a first support ink substrate comprising catalytically inactive supporter particles; providing a first negatively-charged adhesive substrate; and using a 3D printing process to deposit the ink substrates in a predetermined configuration to provide a catalyst structure as described herein.

According to the various embodiments, a single-atom-catalyst system and/or catalyst structure can comprise any necessary or desired shape or geometry. For example, a single-atom-catalyst system or structure can be provided in plate form or cylindrical form, where the plate or cylinder comprises one or more layers comprising the single-atom-catalyst structures or systems described herein.

According to some embodiments, one or more single-atom-catalyst systems described herein may be combined with a reactor apparatus. According to some embodiments, a reactor apparatus may have a fluid inlet and fluid outlet that are in fluid communication the single-atom-catalyst system. Generally speaking, in use, a fluid comprising one or more reactants may be provided through the fluid inlet single-atom-catalyst system. The fluid comprising the reactants can pass through the at least one single-atom-catalyst structure, so that the reactants contact the single-atom-catalyst, and undergo a catalytic reaction to provide a fluid comprising one or more reaction products. The fluid containing the one or more reaction products then exits the reactor at the fluid outlet. The reactor apparatus may comprise a plurality of single-atom-catalyst systems, e.g., in parallel or series.

In certain embodiments of the present disclosure, a single-atom-catalyst structure comprises two single-atom-based catalyst layers for tandem catalysis reactions, such as the direct conversion of methane to ethylene. The ability to use methane as the raw material in the production of ethylene, fuels and other higher value chemicals would be highly advantageous due to the abundance of low cost, domestic natural gas (Ref. 6) and the potential for using biogas in the future. However, because methane's extraordinarily high thermodynamic stability, methane activation remains one of most challenging subjects in heterogeneous catalysis. A reaction of oxidative coupling of methane (OCM) to ethane and ethylene was discovered in the 1980s. (Refs. 7, 8, 9, in Ex. 1) In this reaction, methane is activated heterogeneously on the catalyst surface, forming methyl free radicals, and coupling in the gas phase to form ethane, which subsequently undergoes dehydrogenation to form ethylene. The economic promise of OCM has attracted significant attention in both industry and academic research areas since then. Hundreds of catalysts have been synthesized and examined, but none of these catalytic reactions has achieved the required chemo-selectivity for economic operation. Instead of producing ethylene, the majority of methane is non-selectively oxidized to carbon monoxide and carbon dioxide, or decomposed leading to the formation of coke. The other issue is that ethane is often the major product in current OCM reactions, particularly at the lower temperature range, as it forms first in this reaction.

To overcome the major challenges in the direct conversion of methane to ethylene, the various aspects of the disclosure include new and stable single-atom-based tandem catalysts with unique compositions and structures. Single-atom catalysts possess single-atomically-dispersed catalytic sites on surface of their matrices. Recent research has shown that single-atom catalysts exhibit unique activity and extraordinarily high selectivity as compared to the conventional bulk catalysts. Without being bound by any particular theory, it is believed that single-atom catalysts hold an important key to the improvement of the selectivity and reaction yield in of methane to ethylene conversion. However, single-atom catalysts can often suffer from low thermal stability due to surface diffusion at high temperatures, and low volume loading density associated with their stoichiometry.

In accordance with various embodiments, a single-atom-catalyst system comprises a tandem catalyst structure, i.e., a catalyst system having two catalyst structures provided in tandem relation, as described further herein. Referring to FIGS. 1.4A-1.4C, in accordance with some embodiments, the single-atom-catalyst system comprises a radially-structured tandem catalyst 400 that has a generally cylindrical or tubular structure. While certain embodiments are described with reference to a radially-structured tandem catalyst 400, it will be understood that other geometries, e.g., a plate geometry, can be employed within the scope of the present disclosure. The cylindrical catalyst structure 400 has a longitudinal dimension 401 extending parallel a longitudinal axis from a first end 402 to a second end 403, and a radial dimension or diameter 404 extending radially across a longitudinal centerline 405 of the catalyst to an outer surface 406 of the catalyst. The catalyst structure comprises at least a central fluid conduit 480 that receives a fluid, at least two substantially concentric catalyst layers (430, 460), and an outer annulus 420. Within the catalyst structure, the fluid conduit 480 and concentric catalyst layers 430, 460 and outer annulus 420 are in fluid communication so that a fluid may pass from the central fluid conduit 480 through the concentric catalyst layers 430, 460 to the outer annulus 420. These and other features and aspects of the single-atom-catalyst system and radially-structured tandem catalyst are described in more detail.

In embodiments, the central portion of the cylindrical catalyst 400 is a central fluid conduit 480. The central fluid conduit 480 may be hollow, or it may comprise one or more support structures. For example, the central fluid conduit 480 may have a lattice or honeycomb support structure. According to some embodiments, the central fluid conduit 480 has a diameter measured in the radial direction of from about 0.10 inches to about 0.40 inches, or about 0.15 inches to about 0.35 inches, or about 0.20 inches to about 0.30 inches, or about 0.25 inches.

According to the various embodiments, a first catalyst layer 460 extends radially outward from the central fluid conduit 480. The first catalyst layer 460 comprises a first catalyst structure which comprises an assembly of a plurality of first single-atom-catalyst superparticles. In embodiments, the first single-atom-catalyst superparticles comprise a catalyst for oxidative coupling of methane (OCM) into ethane. The first catalyst structure can be configured to optimize the desired reaction kinetics. For example, the reaction kinetics can be controlled, at least in part, by controlling one or more of the thickness, porosity, density, and distribution of the single-atom active catalytic sites. During use, a fluid will pass through the first catalyst structure and in the presence of the catalyst, constituents of the fluid will react to provide an intermediate fluid.

In some embodiments, the first catalyst layer 460 may further comprise a first support structure 470 intermediate the first catalyst structure and the central fluid conduit 480. The first support structure 470 may support the first catalyst structure. According to some embodiments, the first support structure may comprise a porous layer of $SiO_2$.

In some embodiments, the first catalyst layer 460 may further comprise a first spacer or gap layer 440 extending radially outward from the first catalyst layer 460. After the fluid passes through the first catalyst structure, it may be desirable to provide additional residence time within the catalyst to increase the yield of the reaction catalyzed by the first catalyst, before proceeding further. The first spacer or gap layer 440 has a thickness and/or volume to enable a necessary or desired residence time. The first spacer or gap layer 440 may comprise a support structure or material 450.

According to the various embodiments, a second catalyst layer 430 extends radially outward from the first catalyst layer 460. The second catalyst layer 430 comprises a second catalyst structure comprising an assembly of a plurality of second single-atom-catalyst superparticles. In embodiments, the second single-atom catalyst superparticles comprise a catalyst for oxidative dehydrogenation of ethane (ODE) into ethylene. The second catalyst structure 430 can be configured to optimize the desired reaction kinetics. For example, the reaction kinetics can be controlled, at least in part, by controlling one or more of the thickness, porosity, density, and distribution of the single-atom active catalytic sites. During use, a fluid will pass through the second catalyst structure and in the presence of the second catalyst, constituents of the fluid will react.

In some embodiments, the second catalyst layer may further comprise a second support structure intermediate the second catalyst structure and the first catalyst layer. The second support structure may support the second catalyst structure. According to some embodiments, the second support structure may comprise a porous layer of $SiO_2$.

In some embodiments, an outer annulus 420 may extend radially outward from the second catalyst layer 430. After the fluid passes through the second catalyst layer, it may be desirable to provide additional residence time within the catalyst structure to increase the yield of the reaction catalyzed by the second catalyst. The outer annulus 420 has a thickness and/or volume to enable a necessary or desired residence time.

The radially-structured tandem catalyst 400 may further have a housing 410 that at least partially surrounds and contains the elements of the catalyst. The housing 410 may be integrally formed with the radially-structured tandem catalyst, e.g., a structural layer that is deposited adjacent the outer annulus 420. In alternative embodiments, the housing 410 may be separately provided, e.g., a pre-formed tube that receives the radially-structured tandem catalyst 400. In some embodiments, the housing 410 is configured to be impermeable, e.g., to contain the reactants and reaction products.

According to the embodiments, the radially-structured tandem catalyst 400 has an overall longitudinal dimension 401 of from about 2 inches to about 6 inches, or about 3 inches to about 5 inches, or about 4 inches. According to certain embodiments, the radially-structured tandem catalyst has an overall diameter, measured in the radial direction, from about 1 inch to about 20 inches, from about 1.25 inches to about 1.75 inches, or about 1.50 inches.

One or more radially-structured tandem catalysts described herein may be combined with a reactor apparatus. For example, referring to FIG. 1.4C, according to some embodiments, a reactor apparatus 500 may have a fluid inlet 580 that is in fluid communication with the central fluid conduit 480 of the radially-structured tandem catalyst, and a fluid outlet 520 that is in fluid communication with the outer annulus 420. Generally speaking, in use, a fluid comprising one or more reactants may be provided through the fluid inlet 580 to the central fluid conduit 480 of the radially-structured tandem catalyst 400. The fluid comprising the reactants can pass through the first catalyst layer 460, undergoing a first catalytic reaction to provide a fluid comprising one or more first reaction products. The intermediate reaction products then can pass through the second catalyst layer 430, undergoing a second catalytic reaction to provide a fluid containing one or more second reaction products. The fluid containing the one or more second reaction products then exits the reactor at the fluid outlet 520. The reactor apparatus may comprise a plurality of radially-structured tandem catalysts 400 arranged in parallel or series.

According to certain embodiments, the radially-structured tandem catalysts can be 3D printed from one longitudinal end to another, by depositing layers of pre-determined arrays of the first single-atom-catalyst inks and the second single-atom-catalyst inks to form the first catalyst layer and second catalyst layer, respectively, of the radially-structured tandem catalyst, as described herein. By 3D printing with inks comprising the first and second single-atom-catalyst superparticles, respectively, self-assembly of the superparticles further can form superstructures with controlled porosity with sub-micron precision.

D. REFERENCES

References are cited herein throughout using the format of reference number(s) enclosed by parentheses corresponding to one or more of the following numbered references. For example, citation of references numbers 1 and 2 immediately herein below would be indicated in the disclosure as (Refs. 1 and 2).

Ref 1 (a) Shell has two GTL plants, one in Bintulu, Malaysia and one in Qatar (http://www.shell.com/energy-and-innovation/natural-gas/gas-to-liquids.html), and Sasol (South Africa) is operating two GTL plants (http://www.sasol.com/innovation/gas-liquids/overview)); (b) http://www.prnewswire.com/news-releases/global-ethylene-capacity-and-capital-expenditure-outlook---us-and-china-to-lead-ethylene-industry-expansion-300324140.html; and (c)

Ref. 2 C. Karakaya, R. J. Kee, "Progress in the direct catalytic conversion of methane to fuels and chemicals," *Progress in Energy and Combustion Science* 55 (2016) 60-97.

Ref 3 A. Galadima, O. Muraza, "Revisiting the oxidative coupling of methane to ethylene in the golden period of shale gas: A review," *Journal of Industrial and Engineering Chemistry*, 37 (2016) 1-13.

Ref. 4 http://www.essentialchemicalindustry.org/chemicals/ethene.html.

Ref. 5 http://www.essentialchemicalindustry.org/processes/cracking-isomerisation-and-reforming.html#steam_cracking.

Ref. 6 http://www.eia.gov/naturalgas/.

Ref 7 G. E. Keller, M. M. Bhasin, "Synthesis of Ethylene via Oxidative Coupling of Methane," *Journal of Catalysis* 73 (1982) 9-19.

Ref 8 K. Otsuka, K. Jinno, A. Morikawa, "Active and Selective Catalysts for the Synthesis of $C_2H_4$ and $C_2H_6$ via Oxidative Coupling of Methane," *Journal of Catalysis* 100 (1986)

Ref. 9 T. Ito, J. H. Lunsford, "Synthesis of ethylene and ethane by partial oxidation of methane over lithium-doped magnesium oxide," *Nature* 314 (1985) 721-722.

Ref 10 Trenton W. Elkins, Björn Neumann, Marcus Bäumer, and Helena E. Hagelin-Weaver, "Effects of Li Doping on MgO-Supported $Sm_2O_3$ and $TbO_x$ Catalysts in the Oxidative Coupling of Methane," *ACS Catalysis*, 4 (2014) 1972-1990.

Ref 11 Trenton W. Elkins, Samantha J. Roberts, Helena E. Hagelin-Weaver, "Effects of alkali and alkaline-earth metal dopants on magnesium oxide supported rare-earth oxide catalysts in the oxidative coupling of methane," *Applied Catalysis A* 528 (2016) 175-190.

Ref 12 T. W. Elkins, H. E. Hagelin-Weaver, "Characterization of $Mn$—$Na_2WO_4/SiO_2$ and $Mn$—$Na_2WO_4/MgO$ catalysts for the oxidative coupling of methane," *Applied Catalysis A* 497 (2015) 96-106.

Ref 13 X. Guo, G. Fang, G. Li, et al. "Direct, Nonoxidative Conversion of Methane to Ethylene, Aromatics, and Hydrogen," *Science* 344 (2014) 616-619.

Ref 14 S. F. Hakonsen, J. C. Walmsley, A. Holmen, "Ethene production by oxidative dehydrogenation of ethane at short contact times over Pt—Sn coated monoliths," *Applied Catalysis A* 378 (2010) 1-10.

Ref. 15 P. D. K. Nezhad, M. Haghighi, N. Jodeiri, F. Rahmani, "Sol-gel preparation of $NiO/ZrO_2(x)$-MgO (100-x) nanocatalyst used in $CO_2/O_2$ oxidative dehydrogenation of ethane to ethylene: influence of Mg/Zr ratio on catalytic performance," *Journal of Sol-Gel Science and Technology* 80 (2016) 436-450.

Ref 16 H. Zhu, D. C. Rosenfeld, M. Harb, D. H. Anjum, M. N. Hedhili, S. Ould-Chikh, and J.-M. Basset, "Ni-M-O (M=Sn, Ti, W) Catalysts Prepared by a Dry Mixing Method for Oxidative Dehydrogenation of Ethane," *ACS Catalysis*, 6 (2016) 2852-2866.

Ref 17 (a.) J. Lynch, J. Zhuang, T. Wang, D. LaMontagne, H. Wu, and Y. C. Cao, Gas-Bubble Effects on the Formation of Colloidal Iron Oxide Nanocrystals J. Am. Chem. Soc., 133 (2011), 12664-12674; (b.) J. Park, K. An, Y. Hwang, J. Park, H. Noh, J. Kim, J. Park, N. Hwang and T. Hyeon, Ultra-large-scale syntheses of monodisperse nanocrystals, Nature Materials, 3(2004), 891-895

Before proceeding to the Examples, it is to be understood that this disclosure is not limited to particular aspects described, and as such may, of course, vary. Other systems, methods, features, and advantages of foam compositions and components thereof will be or become apparent to one with skill in the art upon examination of the following drawings and detailed description. It is intended that all such additional systems, methods, features, and advantages be included within this description, be within the scope of the present disclosure, and be protected by the accompanying claims. It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

E. EXAMPLES

Now having described the embodiments of the present disclosure, in general, the Examples describe some additional embodiments of the present disclosure. While embodiments of the present disclosure are described in connection with the Examples and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

This Example demonstrates through the use of combined fields of chemistry, chemical engineering, materials science and physics, the state of the art synthesis of specifically designed complex nanoparticle systems using colloidal synthesis for use as heterogeneous catalysts and the novel reactor design using 3D printing together with reaction engineering measurements, Specifically, this example demonstrates a total-length-scale control approach to design and construction of novel heterogeneous catalysts for direct conversion of natural gas to higher value chemicals. At the atomic scale, lattice-strain engineering was used to control the crystal structure and surface habits of catalyst matrices and to stabilize single-atom catalytic site at high reaction temperatures, which also allowed fine-tuning of the selectivity and activity of these single-atom sites. At the nanometer scale, a nanoparticle self-assembly method was used to control catalyst porosity and to increase the volume density of single-atom catalytic sites in sub-micrometer superparticles. At macroscopic scale, a 3-D printing technique was employed to assemble the superparticles into composite catalyst pellets with sub-millimeter structures, which allowed fine control over reaction kinetics to minimize non-selectively oxidization of methane and to maximize the ethylene production yield.

This total-length-scale control approach is comprehensive for design of functional materials. It can be readily extended for construct the powerful single-atom catalysts for other reactions with extraordinarily high selectivity and activity, as well as reaction kinetics control ability. This advance may open an opportunity to modernize many of conventional catalysts with improved chemoselectivity, allowing the production of daily used chemicals (e.g., food packaging materials, eyeglasses, medical devices, display liquid crystals, lubricants and engine coolants) in a cheaper, greener and energy more efficient manner.

In addition, the disclosed methods and devices potentially make the direct conversion of methane to ethylene economically viable for industrial operation. This can have a significant economic impact, since abundant domestic natural gas can be utilized rather than foreign oil, and this synthesis route have a higher overall energy efficiency and lower greenhouse-gas emission as compared to current ethylene production route using petroleum-based naphtha.

This Example demonstrates synthesis, characterization and optimization of an exemplary single-atom based tandem catalysts at three length scales. The composition of catalytically active component and metal-oxide core-shell nanoparticles were carefully selected. $NiO_x$ and $FeO_x$ were used as nanoparticle cores because their lattice constants can be easily tuned via redox reactions through Kirkendall process. MgO, CaO and $SiO_2$ were used as a support matrix as nanoparticle shells. (Refs. 10, 11, 12) Sm, Fe, Mn, Na, W, Pt, Sn were chosen as catalytically-active components. Specifically, Sm-doped MgO/CaO, Fe-doped $SiO_2$, Mn-doped $SiO_2$ and Na—W doped $SiO_2$ were used as the catalysts for oxidative coupling of methane (OCM) into ethane, (Refs. 11, 12, 13) and Ni-doped $SiO_2$ and Pt—Sn doped $SiO_2$ for subsequent oxidative dehydrogenation of ethane (ODE) into ethylene. (Refs. 14, 15, 16).

Synthesis and Characterization of Single-Atom Catalyst Nanoparticles Through Surface Doping Colloidal Nanoparticles.

Lattice-strain induced by lattice mismatching between core and shell have significant effects on the crystal structure and habit of shell because of surface free energy relaxation of shell materials. $NiO_x$ and $FeO_x$ were chosen as core materials for two reasons: (1) their synthesis procedure has been well-established, and (2) they adopt a cubic lattice structure and their lattice constants can be controlled to about 20% variance, which is ideal for controlling the growth of MgO, CaO and $SiO_2$ shells through lattice-strain engineering. Single-atom catalyst nanoparticles were synthesized in four steps). Referring to FIG. 1.1, first, spherical $NiO_x$ and $FeO_x$ nanoparticles of 10, 20, and 30 nm with size distribution of 5% were synthesized using published procedure. (Ref. 17) Second, MgO, CaO and $SiO_2$, $NiO_x$, $AlO_x$, ZnO, $TiO_x$, Graphene shells with thickness of 3-8 nm were grown onto these cores in octadecene solution using corresponding organometallic precursors. MgO, CaO, $FeO_x$, $AlO_x$, ZnO, $TiO_x$, and Graphene shells were grown on $NiO_x$ cores and $SiO_2$ shell were grown on $FeO_x$ cores because of their chemical affinity and lattice matching level. Third, the resulting shells were annealed in a pure octadecene solution at 320° C. to achieve desired crystalline form, where MgO and CaO shell on $NiO_x$ cores adopted cubic rocksalt structure and $SiO_2$ shell on $FeO_x$ cores displayed a tetragonal α-cristobalite crystal structure. Fourth, the chosen catalytic active materials (Sm, Fe, Mn, Na, W, Pt, and Sn) were used as dopants to growth onto the surface of core-shell nanoparticles. The precursors of these elements were in an organometallic form with bulk ligands comprising ethyl-hexyl or heptyl-undecyl groups. Such bulky ligands can induce entropy effects to prevent the growth of two dopants at neighboring lattice sites of the shell. The number of dopants were controlled by precursor amount. The resulting surface doped nanoparticles were activated to form single-atom catalysts through stepwise pyrolysis of organic binding materials in the presence of oxygen at a temperature of 600-1000° C. over 3-6 hours. These single-atom catalyst nanoparticles were characterized using XRD, XPS, high-resolution TEM and XPS, and their catalytic activity, selectivity and stability in OCM and ODE reactions were monitored using gas chromatography.

Synthesis and Characterization of Single-Atom Catalyst Superparticles.

Superparticles are nanoparticle assemblies in the form of colloidal particles. The choice to make superparticles was for two reasons: (1) nanoparticles are assembled into close packed superlattices can increase the volume loading density of single-atom catalytic sites in a structure with controlled porosity (e.g., superlattices of 25-nm nanoparticles have about 3.8 nm pores), thus leading to an overall high reactivity. (2) The resulting superparticles form stable colloids and they can be used as building blocks in a form of inks to construct structures in a larger scale.

Superparticles of single-atom catalyst nanoparticles were prepared using a two-step method. Referring to FIG. 1.2, in the first step (Ia or Ib), the nanoparticles made in Example 1a, with hydrophobic ligands were passivated with dodecyl trimethylammonium bromide (DTAB) forming nano particle micelles in aqueous solution. In the second step (IIa or IIb), under stirring, the nanoparticle-micelle solution was injected into a flask with ethylene glycol, causing the decomposition of nanoparticle-micelles, and subsequent the aggregation of nanoparticles and the eventual formation of superparticles. Two types of superparticles were synthesized: (a) single-component superparticles with OCM or ODE catalysts (FIG. 1.2A), and (b) binary superparticles with both OCM and ODE catalysts at a controlled ratio (FIG. 1.2B). The size of superparticles was controlled by controlling the amount of DTAB. We made superparticles with passively charged surface and size of 250 nm for the use as inks to print final catalyst pellets. The resulting superparticles were characterized using XRD, XPS, high-resolution TEM and XPS, as well as Brunauer-Emmett-Teller (BET) surface area measurements.

Construction and Characterization of 3-D Printed Catalyst Pellets.

In this Example, we used a 3D printing technique to form a catalyst pellet structure. The inks used in the 3D-printing included certain functional components, as described. Positively charged SAC superparticles made in Example 1b were used as inks for catalysts. Positively charged catalytically inactive supporter particles (200-nm $SiO_2$ nanoparticles) were used as inks for gap support structures and OCM catalyst support structures. Negatively charged polymers such as sodium polyacrylate were used as binder inks. Glass micro-capillaries with 20-μm tips were used for injection. Injection of different inks were controlled by three syringe pumps, and linear translational stages were used to control the location of printing objects. During 3D-Printing, self-assembly of superparticles took place, leading to the formation of superstructures with controlled structural porosity with sub-micron precision. This self-assembly process was controllable by controlling the surface nature of superparticles and chemical nature of binders. The density and average distance between SAC superparticles were controlled by controlling the concentration and surface nature of the catalytically inactive supporter particles in the ink.

Referring to FIG. 1.4A-1.4B, catalyst pellet tubes were printed starting from a bottom cap at the first end 402 of the pellet 400, and continuing layer-by-layer in the longitudinal direction of the pellet to the second end 403 of the pellet. The pellets 400 were configured to have a first catalyst layer 460 comprising an OCM catalyst, and a second catalyst layer 430 comprising an ODE catalyst, with a gap layer 440 intermediate the first catalyst layer 460 and second catalyst layer 430. The pellets 400 were printed to have an outer diameter (404) of 1.5 inches, and a longitudinal dimension (401) of 4 inches, with a central fluid conduit (480) having a diameter of about 0.25 inches. The catalyst pellet tubes 400 were used in a reactor, such as the reactor 500 in FIG. 1.4C. During reaction, gas entered the pellet via the central fluid conduit 480 (see arrows) and flowed radially outward through the catalyst pellet, as shown with the arrows in FIG. 1.4C. In other words, the gas (or its reaction product) flowed through sequential layers. A porous $SiO_2$ layer served as a gas distribution layer as well as a support 470 for the thin OCM catalyst layer 460. A gap layer 440 allowed the methyl radicals generated by the OCM catalyst layer 460 further time to react before entering the ODE catalyst layer 430 and reacting form ethylene which flowed out via the annulus 520 formed between the reactor housing 410 and the catalyst pellet tube, and the reaction product comprising ethylene flowed from the reactor at fluid outlet 520. These radial-structured catalysts allowed fine control over reaction kinetics by designer's dynamic feeding procedures, such as, cycles of the following; (1) Continuous flow of $O_2$ (for catalyst activation); (2) $He_2$ for purging excess $O_2$, and (3) $CH_4$ for conversion reaction, as this operation limited the existence free $O_2$ and thus minimized the formation of CO and $CO_2$ in the conversion reaction.

The performance of the exemplary catalyst pellet outperformed with the performance of a 3D printed catalyst pellet tube with only a catalyst support structure and gas distribution layer and a catalyst layer composed of mixed OCM and ODE catalysts.

Example 2. Synthesis of Iron-Oxide Nanocrystals as Core

Synthesis of iron-oleate precursor. Iron chloride (10.8 g, 40 mmol) was first dissolved in a mixture of 80 mL ethanol and 60 mL Nanopure® water in a three-neck flask (500 mL). Afterwards, sodium oleate (36.5 g 120 mmol) was quickly added to the iron chloride solution along with 140 mL hexane. The resulting solution was allowed to stir until the sodium oleate was completely dissolved. Next, the reaction solution was heated to reflux for 4 hours. When the reaction was finished and cooled to room temperature, the upper organic layer containing the iron oleate was washed three times with 30 mL of Nanopure® water in a 250 mL separatory funnel. Excess hexane was then evaporated using a rotovap. The resulting iron oleate was transferred into a 100 mL round bottom flask and connected to a Schlenk line where it was placed under a vacuum of about 25 mtorr overnight, and then the iron oleate was well sealed in a glass vial and stored in a desiccator for two days of aging. The reaction yield of iron oleate was about 90%.

Synthesis of 6-nm Iron Oxide Nanocrystals. Iron oleate (5.0 mmol, 4.5 g) and oleic acid (2.5 mmol, 0.75 g) were added into a three-neck flask (100 mL) with a solvent mixture of ODE (25.0 g). The mixture was heated to 120° C. and was pumped for 1 hour, and the mixture was purged with argon. Under an argon flow, the reaction solution was heated to 320° C. at a heating rate of 3.0° C./min. Reaction time was counted from the moment when 320° C. was reached. After 30-min reaction, the reaction solution was quickly cooled to room temperature by blowing air across the reaction flask. The resulting nanocrystals were precipitated using acetone, and then were purified using three rounds of precipitation/redispersion cycles with acetone and hexane as the solvents. After purification, the product was dispersed in nonpolar solvents such as hexane or toluene. A transmission electron microscope (TEM) image of representative iron-oxide nanocrystals 500 is shown in FIG. 1.5.

Example 3. Synthesis of Sm-Doped $Fe_3O_4$/MgO Core/Shell Nanocrystals

Surface-doped iron-oxide/magnesium oxide core/shell nanocrystals were synthesized in two steps. In the first step, a hexane solution of iron-oxide nanocrystals (6.0 nm in diameter, 4.0 g) was mixed with a 15-mL octadecene solution containing 1,2-tetradecanediol (4 mmol), oleic acid (4 mmol) and oleylamine (4 mmol), and hexane was removed via pumping at room temperature. Under an argon flow, the resulting solution was heated to 305° C., and then an octadecene solution containing magnesium 2-ethylhexanoate (0.05 mM) was added in dropwise, forming iron-oxide/magnesium-oxide core/shell nanocrystals. When a desired shell thickness was achieved, the reaction solution was heated to 320° C. and aged for 30 min. In the second step, an octadecene solution of samarium(III) 2-ethylhexanoate (0.05 micron molar, at amount of a doping level of 10-15 samarium atoms per nanocrystals) was added dropwise into the reaction solution, forming doped $Fe_3O_4$/MgO core/shell nanocrystals with samarium at their surface. The resulting solution was further aged for 1 hour, and then was cooled to room temperature over a period time of about 20 min. The resulting Sm-doped $Fe_3O_4$/MgO core/shell nanocrystals were precipitated using ethanol, and then were purified using two rounds of precipitation/redispersion cycles with ethanol and chloroform as the solvents. After purification, the product was dispersed in chloroform for further use. TEM images of representative nanocrystals 600 are shown in FIG. 1.6.

Example 4. Synthesis of Superparticles with Sm-Doped $Fe_3O_4$/MgO Core/Shell Nanocrystals DTAB (20.0 mg, 65.0 μmol) was dissolved in Nanopure water (1.0 mL) to form a solution. A chloroform solution of Sm-doped $Fe_3O_4$/MgO nanoparticles (30 μM, 1.0 mL) was thoroughly mixed with the DTAB solution by a vortex mixer. Afterwards, the chloroform was removed from the mixture by bubbling argon at 35° C., yielding a clear superparticle aqueous solution. Then a 3-mL aqueous of polvinylpyrrolidone (PVP, 2.0 mM, MW=55,000) was added into the superparticle solution, and the resulting solution was further stirred for 30 min. The resulting colloidal superparticles were separated by centrifuge (500 g, 15 min). The black precipitate was re-dispersed into ethanol and the superparticles were further purified twice through centrifugation and dispersed in water for future use. A TEM image of representative superparticles is shown in FIG. 1.7, which shows exemplary assemblies of nanoparticles 710 into superparticles 720.

Example 5. Ligand-Programmed Assembly of Hydrophobic Nanoparticles in a Spherically Confined System Introduction to Example 5

Superparticles are collections of artificial atoms in the form of colloidal particles. These superparticles can be used individually or as building blocks to construct materials with designed hierarchical superstructures for a given application. Superparticles can be synthesized in spherically confined systems through either solvent evaporation or solvent-induced decomposition of nanoparticle micelles. Superparticles with spherical building block nanoparticles adopt either an icosahedral (IC) or a face-centered cubic (fcc) structure. Spherical confinement from emulsion droplets is important to the formation of IC superparticles. There exists a superparticle-size-dependent IC-fcc transition. The phase-transition size is dependent on the interparticle bonding energy of building block nanoparticles. The higher the interparticle bonding energy, the larger the transition size, and the larger the stable size for IC superparticles. Importantly, the interparticle bonding energy of given nanoparticles can be encoded with predesigned surface ligand packing configurations. This advance allows one to control the symmetry of superparticles between an IC and an fcc structure through ligand-programmed nanoparticle assembly.

Discussion of Example 5

The assembly of nanoparticles has emerged as a new approach for constructing materials with desired properties for given applications.[12] Nanoparticle assemblies can lead to the formation of superparticles and superlattices with extended networks. Superparticles, comprising nanoparticle superlattices in closed systems, are collections of nanoparticles in the form of colloidal particles.[3] These superparticles exhibit properties similar to their counterparts in extended networks.[3-5] They can be used individually, or as building blocks to construct materials with predesigned hierarchical superstructures, whereby new properties can be further introduced by tailoring the complex inter-nanoparticle interactions inside these superstructures.[3] To date, there has been growing interest in developing strategies that can be used to organize nanoparticles of all types into well-defined lattices inside closed systems.[6-12]

Two successful methods have been developed to synthesize superparticles with high supercrystalline quality.[6, 7] Both methods utilize emulsion droplets as closed systems to confine the growth of nanoparticle superlattices. One method is based on solvent-induced decomposition of nanoparticle micelles (SIDN), and the other is through solvent evaporation of nanoparticle solutions inside emulsion droplets.[6, 7] These two methods have led to the synthesis of a number of different types of superparticles from spherical nanoparticles, nanocubes, and nanorods as building blocks.[6-18] Collective-effect-induced enhancement of photoluminescence polarization ratios has been identified in superparticles of CdSe/CdS nanorods.[4] Shape-dependent cytotoxicity was found in superparticles of nanocubes.[11] Magneto-fluorescent core/shell superparticles have been made for use as dual-modal imaging probes for in vivo multi-photon and magnetic resonance imaging.[15]

Based on the solvent-evaporation method, a number of research groups have found that superparticles of spherical nanoparticles or nanocubes with rounded corners can exhibit a 20-fold twinned icosahedral (IC) structure.[5, 10, 12, 14, 17, 19, 20] Lacava et al. proposed that the formation of IC superparticles of gold nanoparticles is mainly due to energetic interactions between these building block nanoparticles.[10] In a seminal paper, de Nijs et al. reported a systematic study on the formation of IC superparticles from 6-nm cobalt-iron-oxide nanoparticles.[12] Their experimental results have shown that resulting superparticles can adopt either an IC symmetry or a single-domain face-centered cubic (fcc) symmetry. The symmetry choice is dependent upon the size of superparticles (or the number of building block nanoparticles): nearly all the superparticles with less than 20,000 nanoparticles adopt an IC symmetry, while superparticles containing more than 90,000 nanoparticles exhibit solely fcc ordering.[12] Their molecular dynamics simulations of hard sphere assembly in a shrinking spherical box have shown excellent agreement with experimental observations. They have made a strong statement that the formation of IC superparticles in spherical confinement is purely entropy-driven, and that it is not simply a kinetic, but rather an equilibrium effect.[12] However, some of these results are not quite consistent with our previous studies. We have shown that 165-nm superparticles of 5.8-nm iron-oxide nanoparticles can be made in a size-controlled fashion using the SIDN method.[7,8] These superparticles adopt a single-domain fcc structure, but their building block number is only ~5700, which locates deeply inside the stable size regime of IC particles observed by de Nijs et al. This inconsistency brings up a question of whether the formation of IC superparticles is a purely entropy-driven process in these syntheses. We hypothesize that this inconsistency is caused by the different strengths of interparticle interactions in these two sets of experiments. The interparticle interactions were stronger in the de Nijs' experiments than in ours, thus leading to the formation of larger sized IC superparticles, which were not observed in our previous experiments. This hypothesis is consistent with the results from our studies on shape-controlled synthesis of superparticles from nanocubes, which have shown that stronger interparticle interactions introduced by a higher ligand grafting density lead to the formation of cube-shaped superparticles, whereas superparticles adopt a spherical shape when interparticle interactions were relatively weaker due to a lower ligand grafting density.[11]

To test this hypothesis, we have used the solvent-evaporation method to perform superparticle synthesis from 9.0-nm iron-oxide nanoparticles with oleic acid (OA) ligand grafting densities (ligand per $nm^2$) of 2.54, 2.87, and 3.38 (FIG. 2.1a and Table S1, supporting information). Please note that all the iron-oxide nanoparticles used in this work were prepared in the same synthesis, and ligand grafting density was varied through ligand exchange. We have also performed the nanoparticle assembly at the air-liquid interface and air-solid interface as control experiments to evaluate the quality of these nanoparticles (FIGS. 2.1 and 2.7, supporting information).[21] Solvent-evaporation-based synthesis often leads to superparticle samples with very poor size distributions because emulsions are thermodynamically very unstable systems. We have achieved superparticle synthesis in a size-controlled manner using a home-made system which allows for fine control over experimental parameters such as evaporation flow rate, stirring speed, etc. (FIG. 2.5, supporting information). Resulting superparticles were characterized using transmission electron microscopy (TEM), and they exhibit sizes ranging from 91.2 nm to 483.5 nm with size distributions of 10-20% (FIG. 2.6, supporting information).

Our TEM observations have shown that nanoparticle packing symmetry in superparticles of ~225 nm (~5700 building block nanoparticles) is strongly dependent on their ligand grafting density. With the increase of ligand grafting density, resulting superparticles adopt an amorphous, an fcc, and an IC structure (FIG. 2.1c-e). (We name the corresponding building block nanoparticles as AM, $fcc_1$ and $IC_{OA}$, respectively). The formation of fcc superparticles (containing ~5700 nanoparticles) is consistent with our previous results from the superparticles synthesized using the SIDN method,[7, 8] indicating that the superparticle symmetry might not be affected by the synthesis method. In addition, these data support our hypothesis that interparticle interactions play a major role in the formation of superparticles.

In our experiments, the structural integrity of each superparticle is carefully examined through systematically tilting the specimen in TEM. An IC structure consists of 20 equisized tetrahedral subunits. The subunits join together on adjacent bounding faces (twin faces) and enclose an angle of $\sim 2\pi/5$.[22, 23] The nanoparticle packing arrangements in an IC superparticle are examined along four characteristic orientations using a double-tilt specimen holder.[23] With a 5-fold axis parallel to TEM beam, 10 twin subunits are seen in the TEM image, and its fast Fourier transform (FFT) pattern shows characteristic 10-fold symmetry reflection spots (FIG. 2.2a).[23] With one tetrahedral face resting on the substrate, one 3-fold axis of this IC particle is parallel to the beam, six twin subunits are visible in the TEM image, and its FFT pattern shows the characteristic reflection spots of 6-fold symmetry (FIG. 2.2b).[23] The TEM images of this IC particle tilted in the other two characteristic orientations are shown in FIGS. 2.2c and 2.2d, and the corresponding FFT patterns exhibit the expected reflections characteristic of IC symmetry.[23] Due to the limits of instrumentation, the structural integrity of an fcc superparticle is examined along either the [001] and [011] zones or the [111] and [211] zones through specimen tilting (FIG. 2.2e-h).

Interestingly, these three types of nanoparticles (AM, $fcc_1$ and $IC_{OA}$) can form large-sized superlattices with extended networks with a single super-crystalline fcc structure when they were crystalized at the air/liquid interface (FIG. 2.1f-h). This suggests that the spherical confinement of emulsion droplets is important to the formation of IC structure. In addition, interparticle interactions and interaction homogeneity can be tailored by surface ligand functionalization (FIGS. 2.7 and 2.8, supporting information). We further hypothesize the observed ligand-density-induced increase of interparticle-interaction strengths is due to the formation of "effective bonding domains" through the interdigitation between hydrocarbon chains of oleic acid ligands from neighboring nanoparticles (FIG. 2.8, supporting information). Therefore, nanoparticles with ligand densities that allow for the formation of "effective bonding domains" exhibit strong interparticle interactions.

Based on the optimal packing model (OPM),[24] we have used ligand density of $IC_{OA}$ nanoparticles to estimate the average bonding energy of "effective bonding domains," which give rise to interparticle bonding energies in the range of 4.1~49 $k_bT$ at 298 K (FIG. 2.9 and Table S2, supporting information). Such bonding energies are larger than the van der Waals forces between neighboring nanoparticle cores, and they are certainly sufficient to introduce a profound effect on both the kinetics and thermodynamics of the nucleation and growth of superparticles inside emulsion droplets, thus leading to the formation of IC superparticles (FIG. 2.1). In contrast, when ligand density is low in the case of $fcc_1$ nanoparticles, "effective bonding domains" could not form although interparticle spacing is closer, resulting in weaker interparticle interactions, thus the formation of fcc superparticles (FIG. 2.1).

The ligand density of $IC_{OA}$ nanoparticles is associated with 67.6% surface coverage, thus there is still some room to further increase the number of OA ligands onto these nanoparticles. We speculate that, when the ligand density is higher than a critical number, the hydrocarbon chain interdigitation between neighboring nanoparticles could be substantially suppressed by steric hindrance effects. This can result in weaker interparticle interactions, and the possible formation of fcc superparticles (FIG. 2.3a,b,e). To examine this possibility, we have further loaded OA ligands onto $IC_{OA}$ nanoparticles, yielding nanoparticles with a surface ligand coverage of 81.4% (Table S1). TEM observations have shown that the resulting nanoparticles exhibit an interparticle spacing of 3.8 nm in the monolayers formed on a carbon grid, which is 1.1 nm larger than that between the $IC_{OA}$ nanoparticles (FIG. 2.7, supporting information). Such an increase of interparticle spacing could lead to a substantial decrease of interparticle bonding energy during nucleation and growth of superparticles. Indeed, superparticles made of these nanoparticles solely adopt an fcc structure (FIG. 2.3g).

This result is consistent with the mechanism of ligand-density-induced suppression of hydrocarbon chain interdigitation between neighboring nanoparticles. If this mechanism is truly valid, then there would be a case that when loading ligands with a chain length different from that of OA ligand onto $IC_{OA}$ nanoparticles, hydrocarbon chain interdigitation would not be substantially suppressed, because some configurations of mixing ligands allow hydrocarbon chain interdigitation (FIG. 2.3c,d). To examine this possibility, we used octanoic acid (OcA) as a shorter ligand, and 12-cholesteroxy-12-oxododecanoic acid (CODA) as a longer ligand to modify $IC_{OA}$ nanoparticles.

The resulting OA/OcA and OA/CODA mixture coated nanoparticles exhibit interparticle spacings in their monolayers formed on carbon grids of 2.8 nm and 4.8 nm, respectively. OA/OcA capped nanoparticles exhibit a ligand-interpenetrating level which is very close to that of the $IC_{OA}$ nanoparticles, while bearing a higher density of ligands. This would lead to slightly higher interparticle bonding energies than those between $IC_{OA}$ nanoparticles. A CODA molecule has a length of 3.48 nm, therefore, the 4.8-nm interparticle spacing is associated with a much higher interpenetration level than that in $IC_{OA}$ nanoparticles, which can result in stronger interparticle interactions. Both cases should favor the formation of IC superparticles. Amazingly, TEM observations indeed showed that the superparticles of both of these nanoparticles solely adopt an IC symmetry (FIG. 2.3h,i). These results, together with those from superparticles formed from nanoparticles with only OA ligands, strongly suggest that (1) energic interactions play an important role in controlling the nanoparticle packing symmetry of superparticles, and (2) energic interactions largely originate from the interdigitation of hydrocarbon chains from neighboring nanoparticles (in the text here, ligand interpenetration provides an opportunity for the formation of effective bonding via interdigitation of ligand hydrocarbon chains).

To evaluate the size dependence of the superparticle symmetry in more detail, we have systematically characterized the superparticles from samples synthesized using all six building block nanoparticles discussed above (the three nanoparticles prepared from $IC_{OA}$ nanoparticles are labeled as $fcc_2$, $IC_S$ and $IC_L$, see FIG. 2.4). For superparticle samples made from each of these building blocks, we have examined about 230 superparticles with diameters in the range of 70 nm to 570 nm (containing between approximately 55 and 90,000 nanoparticles). Our results show that superparticles synthesized using AM nanoparticles adopt an amorphous structure within the entire size range that we examined here (FIG. 2.4). Superparticles made of the other five types exhibit an IC symmetry at smaller sizes and an fcc symmetry at larger sizes (FIGS. 2.4 and 2.11-2.15, supporting information).

There is a clear transition from an IC to an fcc symmetry in a specific size range for each type of superparticle (FIG. 2.4). Our results also show that this transition size range is dependent on the surface functionalization of building block nanoparticles, hence the interparticle bonding energy as we proposed here (FIG. 2.4). Based on our estimation using the OPM model, the interparticle bonding energy order for these building block nanoparticles is $fcc_2 < fcc_1 < IC < IC_S < IC_L$. We can therefore establish a qualitative relationship between transition size and bonding energy. The lower the bonding energy, the smaller the transition size, and vice versa. In other words, the higher the interparticle bonding energy, the larger the stable size for superparticles with an IC symmetry. The lower the interparticle bonding energy, the smaller the stable size of superparticles (FIG. 2.4). The smallest fcc superparticles (80 nm in diameter, containing ~360 particles) identified here are from samples made of $fcc_2$ nanoparticles (FIGS. 2.4 and 2.13, supporting information). The largest IC superparticles (480 nm in diameter and containing ~55,300 nanoparticles) found here are from samples made of $IC_L$ nanoparticles.

The existence of a size-dependent IC-fcc transition is consistent with the experimental data from de Nijs et al.[12] However, our result that IC-fcc transition size is dependent on nanoparticle surface functionalization is inconsistent with the theoretical simulations from de Nijs et al.[12] This result cannot be explained only with an entropy-driven process and an equilibrium effect. Our results suggest that building block nanoparticles used in our experiments as well as in those of de Nijs et al. cannot be simply treated as "hard spheres." There should be significant enthalpic contributions from energetic interactions between these nanoparticles, which leads to experimental results far from the theoretical simulations by de Nijs et al. For example, our results show that superparticles made of $fcc_2$ building block nanoparticles exhibit a stable fcc phase when the building block number is larger than ~1500 (FIGS. 2.4 and 2.13), vs. ~90,000 in the work of de Nijs et al.[12]

In conclusion, our results show that energetic interactions play an important role during the nucleation and growth of superparticles inside emulsion droplets. The spherical confinement of emulsion droplets is important for the formation of IC superparticles. Energetic interactions between nanoparticle building blocks can stabilize the IC symmetry of superparticles to a larger size. A higher interparticle bonding energy leads to the formation of a larger-sized IC superparticle. This seems to match well with observations on large-sized IC structures formed with much stronger metallic and covalent bonds. For example, one has synthesized 250-nm IC silver nanoparticles containing $10^8$ atoms,[25] and 20-μm boron suboxide IC crystals containing $10^{14}$ atoms,[26] where the strong bonding energies between atomic building blocks are essential for the stabilization of these structures.[23] Our results show that the interparticle bonding energy of nanoparticles can be encoded with predesigned surface ligand configurations, which allows for control over the symmetry of resulting superparticles between the IC and fcc ordering in a programmable manner. In addition, our results may indicate that the nuclei of superparticles preferentially adopt an IC structure.[27, 28] Subsequently, these IC nuclei can either grow larger, or go through a phase transition into an fcc structure during growth. The spherical confinement of the emulsion droplets and energetic interactions together play some role in blocking this IC-fcc phase transition, resulting in IC superparticles as observed experimentally. There still remains a challenge on how to take the entropy effect quantitatively into this process. This requires further careful studies from both the experimental and theoretical sides of our research community.

REFERENCES FOR EXAMPLE 5

[1] M. R. Jones, N. C. Seeman, C. A. Mirkin, Science 2015, 347, 6224.
[2] M. A. Boles, M. Engel, D. V. Talapin, Chem. Rev. 2016, 116, 11220.
[3] T. Wang, D. LaMontagne, J. Lynch, J. Q. Zhuang, Y. C. Cao, Chem. Soc. Rev. 2013, 42, 2804.
[4] T. Wang, J. Zhuang, J. Lynch, O. Chen, Z. Wang, X. Wang, D. LaMontagne, H. Wu, Z. Wang, Y. C. Cao, Science 2012, 338, 358.
[5] Y. Yang, B. Wang, X. Shen, L. Yao, L. Wang, X. Chen, S. Xie, T. Li, J. Hu, D. Yang, A. Dong, J. Am. Chem. Soc. 2018, 140, 15038.
[6] F. Bai, D. Wang, Z. Huo, W. Chen, L. Liu, X. Liang, C. Chen, X. Wang, Q. Peng, Y. Li, Angew. Chem. Int. Ed. 2007, 46, 6650.
[7] J. Zhuang, H. Wu, Y. Yang, Y. C. Cao, J. Am. Chem. Soc. 2007, 129, 14166.
[8] J. Zhuang, H. Wu, Y. Yang, Y. C. Cao. Angew. Chem. Int. Ed. 2008, 47, 2208.
[9] J. Zhuang, A. D. Shaller, J. Lynch, H. Wu, O. Chen, A. D. Q. Li, Y. C. Cao, J. Am. Chem. Soc. 2009, 131, 6084.
[10] J. Lacava, P. Born, T. Kraus, Nano Lett. 2012, 12, 3279.
[11] T. Wang, X. Wang, D. LaMontagne, Z. Wang, Z. Wang, Y. C. Cao, J. Am. Chem. Soc. 2012, 134, 18225.
[12] B. de Nijs, S. Dussi, F. Smallenburg, J. D. Meeldijk, D. J. Groenendijk, L. Filion, A. Imhof, A. van Blaaderen, M. Dijkstra, Nat. Mater. 2015, 14, 56.
[13] P. Li, Q. Peng, Y. Li, Adv. Mater. 2009, 21, 1945.
[14] D. Wang, M. Hermes, R. Kotni, Y. Wu, N. Tasios, Y. Liu, B. de Nijs, E. N. van der Wee, C. B. Murray, M. Dijkstra, A. van Blaaderen, Nat. Commun. 2018, 9, 2228.
[15] O. Chen, L. Riedemann, F. Etoc, H. Herrmann, M. Coppey, M. Barch, C. T. Farrar, J. Zhao, O. T. Bruns, H. Wei, P. Guo, J. Cui, R. Jensen, Y. Chen, D. K. Harris, J. M. Cordero, Z. Wang, A. Jasanoff, D. Fukumura, R. Reimer, M. Dahan, R. Jain, M. G. Bawendi, Nat. Commun. 2014, 5, 5093.
[16] P. Wang, Q. Qiao, Y. Zhu, M. Ouyang, J. Am. Chem. Soc. 2018, 140, 9095.
[17] J. Wang, C. F. Mbah, T. Przybilla, B. A. Zubiri, E. Spiecker, M. Engel, N. Vogel, Nat. Commun. 2018, 9, 5259.
[18] R. Shi, Y. Cao, Y. Bao, Y. Zhao, G. Waterhouse, Z. Fang, L. Wu, C. Tung, Y. Yin, T. Zhang, Adv. Mater. 2017, 29, 1700803.
[19] J. Wang, C. F. Mbah, T. Przybilla, S. Englisch, E. Spiecker, M. Engle, N. Vogel, ACS Nano 2019, 13, 9005.
[20] D. Wang, T. Dasgupta, E. B. van der Wee, D. Zanaga, T. Altantzis, Y. Wu, G. M. Coli, C. B. Murray, S. Bals, M. Dijkstra, A. van Blaaderen, Nat. Phys. 2020. https://doi.org/10.1038/s41567-020-1003-9
[21] A. Dong, J. Chen, P. M. Vora, J. M. Kikkawa, C. B. Murray, Nature 2010, 466, 474.
[22] A. L. Mackay, Acta. Crystallogr. 1962, 15, 916.
[23] H. Hofmeister, Encycl. Nanosci. Nanotech. 2004, 3, 431.
[24] U. Landman, W. D. Luedtke, Faraday Discuss. 2004, 125, 1.
[25] M. R. Langille, J. Zhang, M. L. Personick, S. Li, C. A. Mirkin, Science 2012, 337, 954.
[26] H. Hubert, B. Devouard, L. A. J. Garvie, M. O'Keefe, P. R. Buseck, W. T. Petuskey, P. F. McMillan, Nature, 1998, 391, 376.
[27] F. C. Frank, Proc. R. Soc. Lond. A. 1952, 215, 43.
[28] J. Taffs, C. P. Royall, Nat. Commun. 2016, 7, 13225.

Supporting Information for Example 5

Materials and Methods:

Chemicals. Iron chloride hexahydrate (99%), oleic acid (90%), 1-octadecene (ODE, 90%), cholesterol (99%), dodecanedioic acid (99%), dodecyltrimethylammonium bromide (DTAB, 98%), diethylene glycol (99%), and Luviquat™ FC550 (40% in water) were purchased from Sigma-Aldrich; sodium oleate (97%) was purchased from TCI America; magnesium sulfate anhydrate ($MgSO_4$, certified), hexanes (HPLC), chloroform (HPLC), dichloromethane (HPLC), ethanol (200 proof), and acetone (HPLC) were purchased from Fisher Scientific. All chemicals were used without further purification. Nanopure® water was made by an in-house Barnstead Nanopure Diamond System (18.2 MΩ·cm).

Synthesis of iron oleate precursor. Iron oleate precursor was synthesized according to a reported literature method with slight modification.[1] Iron chloride hexahydrate (10.8 g, 40.0 mmol) was dissolved in Nanopure water (60.0 mL) and ethanol (80.0 mL) in a 500 mL flask. After fully dissolving the iron chloride, sodium oleate (36.5 g, 120 mmol) was then added along with hexane (140 mL). Under vigorous stirring, the mixture was heated to 60° C. and refluxed for 4 hours. After the solution cooled to room temperature naturally, the colorless water/ethanol phase was discarded in a separatory funnel. The organic phase was washed by Nanopure water three times, and the solvent was removed via rotovap. The resulting dark red viscous liquid was diluted with 1:1 (w/w) ODE before being vacuumed in a Schlenk line overnight.

Synthesis of iron oxide nanoparticles. Iron oxide ($Fe_3O_4$) nanoparticles were synthesized with a modified literature method.[1] Iron oleate precursor (36.0 g, 20.0 mmol), oleic acid (3.52 g, 12.5 mmol), and ODE (82.0 g) was charged into a 250 mL 3-neck flask and connected to a Schlenk line. The solution was vacuumed three times at room temperature, then vacuumed 1 hour at 80° C. The solution was then heated to 320° C. at 3° C.·min$^{-1}$ and maintained at 320° C. for 30 min before being cooled down to room temperature naturally. 100 mL chloroform and 400 mL acetone were added, and the mixture was centrifuged at 3300 rpm for 10 min. The precipitate was then washed two more times with chloroform and acetone. The nanoparticles were dispersed in an oleic acid:chloroform 1:1 (v/v) mixture at a concentration of 20 mg·mL$^{-1}$, and heated at 85° C. for 2 hours. The acid-treated $Fe_3O_4$ nanoparticles were then washed with acetone once and redispersed in chloroform.

Ligand density control. $Fe_3O_4$ nanoparticles were dissolved in chloroform at a concentration of 10 mg·mL-1 and washed with chloroform and acetone seven times. After extensive purification, $Fe_3O_4$ nanoparticles were redispersed in chloroform at a concentration of 10 mg·mL$^{-1}$ containing the desired amount of oleic acid (0.0 mg·mL$^{-1}$, 0.3 mg·mL$^{-1}$, and 1.5 mg mL$^{-1}$ for AM, $fcc_1$, and $IC_{O4}$, respectively). The mixture was stirred at room temperature for 2 hours, and washed once with acetone before superparticle synthesis. For $fcc_2$, $IC_S$, and $IC_L$ nanoparticles, $fcc_1$ nanoparticles were dispersed in chloroform at a concentration of 10 mg·mL$^{-1}$ containing the desired amount of ligands (3.0 mg·mL$^{-1}$ oleic acid, 1.5 mg·mL$^{-1}$ octanoic acid, and 6.3 mg·mL$^{-1}$ CODA for $fcc_2$, $IC_S$, and $IC_L$, respectively). The mixture was stirred at room temperature for 2 hours, and washed once before superparticle synthesis.

Synthesis of superparticles. The controllable parameters for size selective $Fe_3O_4$ superparticle synthesis include the absolute volume of water and chloroform, the volume ratio between water and chloroform, air flow rate, vortex speed, initial nanoparticle concentration, surfactant concentration, and temperature. For a typical superparticle synthesis, $Fe_3O_4$ nanoparticles were dispersed in chloroform at a concentration of 5 mg·mL$^{-1}$. $Fe_3O_4$ nanoparticle solution (0.5 mL) was then mixed with a DTAB water solution (10 mg·mL$^{-1}$, 0.5 mL). The mixture was stirred vigorously with a vortexer at 2800 rpm, and air was blown into the vial at 30 mL·min$^{-1}$ to evaporate any chloroform in less than 20 min. During the process, the temperature was maintained manually at 35° C. by blowing warm air over the system using a heating gun. The temperature was measured by an infrared thermometer. The synthesized superparticles were then mixed with 1 mL 0.4% FC550 water solution and washed with water two times before characterization.

Synthesis of nanoparticle superlattices. Nanoparticle superlattices were synthesized by solvent evaporation on liquid subphase.[2] $Fe_3O_4$ nanoparticles with the desired ligand coverage were dispersed in a hexanes and chloroform mixture (1:1, v/v) at a concentration of 5 mg·mL$^{-1}$. 50 μL of the above nanoparticle solution was dropped carefully on the surface of diethylene glycol in a Teflon vial with a glass slide cover. The vial was kept at room temperature for more than 2 hours to allow for the evaporation of any non-polar solvent, and the superlattice membrane was transferred to a TEM carbon grid for characterization.

Synthesis of 12-cholesteroxy-12-oxododecanoic acid (CODA). Cholesterol (3.86 g, 10.0 mmol), dodecanedioic acid (6.91 g, 30 mmol), and iron chloride hexahydrate (27.0 mg, 0.1 mmol) were mixed in a 100 mL 3-neck flask. The flask was then connected to a Schlenk line, and heat was applied with a heating mantle to melt the solid reactant at 150° C. After heating for 8 hours with frequent pumping to remove any water produced from the reaction, the flask was cooled down naturally to room temperature. The brownish solid was then dissolved with dichloromethane and dried with $MgSO_4$. The insoluble unreacted dodecanedioic acid was removed together with $MgSO_4$ by filtration, and the solvent was evaporated by rotovap. The residue was purified by silica gel column chromatography eluted with hexanes/ethyl acetate (10:1, v/v) to give CODA in 70% yield as white solid. $^1$H NMR (300 MHz, $CDCl_3$): δ 5.36 (1H), 4.55-4.66 (1H), 2.24-2.37 (6H), 1.78-2.08 (5H), 0.85-1.68 (49H), 0.66 (3H).

TEM and STEM characterization. The size of $Fe_3O_4$ nanoparticles and the size and structure of superparticles were characterized by a Thermo Fisher Scientific™ Talos™ F200i S/TEM operating at 200 kV equipped with a double-tilt specimen holder in conventional transmission electron microscope (TEM) or scanning transmission electron microscope (STEM) modes.

Determination of ligand coverage. The surface ligand coverage was measured by thermogravimetric analysis (TGA). The measurement is performed with a TA Instruments® TGA-Q5000 equipped with a platinum sample holder purchased from DSC Consumables Inc. The sample was dried under reduced pressure (30 mTorr) overnight before transfer to the sample pan and heated from room temperature to 600° C. with a heating rate of 20° C.·min$^{-1}$ in air. The ligand coverages were calculated as grafting density (σ) based on reported literature using equation S-1:[3,4]

$$\sigma = \left[\left(1 - \frac{2 \cdot MW_{Fe_3O_4}}{3 \cdot MW_{Fe_2O_3}} \text{wt \%}\right)\rho_{core}d_{core}N_A\right] / \left[6\left(\frac{2 \cdot MW_{Fe_3O_4}}{3 \cdot MW_{Fe_2O_3}} \text{wt \%}\right)MW_{ligand}\right] \quad \text{(S-1)}$$

where wt % is the remaining weight percentage; $\rho_{core}$ is the density of nanoparticle core, which for $Fe_3O_4$ is 5.17 g·cm$^{-3}$; $d_{core}$ is the diameter of nanoparticle; $MW_{Fe_2O_3}$, $MW_{Fe_3O_4}$, and $MW_{ligand}$ are the molecular weight for $Fe_2O_3$, $Fe_3O_4$, and surface ligand (oleic acid), respectively.

Estimation of interparticle bonding energy due to "effective bonding domains". FIG. 2.9 is a schematic of the interpenetrating cone between two nanoparticles, r and $d_{core}$ are the radius and diameter of nanoparticle, respectively, L is the actual ligand length, and l is the effective ligand length. $A_0$ and $A_l$ are the interpenetration cone bonded area at the nanoparticle surface and the middle of the gap, and $d_{nn}$ is the interparticle distance. Since ligand molecules have a grafting density of 5 ligands-nm-2 when close-packed based on reported literature,[5] with the actual grafting density from TGA, the interparticle distance could be calculated using equation S-2:[6]

$$d_{nn} = 2r\left(1 + \frac{3}{5}\sigma\frac{L}{r}\right)^{\frac{1}{3}} \quad (S\text{-}2)$$

and the interpenetrating cone bonded area $A_0$ and $A_L$ could be calculated using equation S-3 and S-4:

$$A_0 = \Omega r^2 = 2\pi\left[1 - \frac{r\left(1 + \frac{3}{5}\sigma\frac{L}{r}\right)^{\frac{1}{3}}}{r+L}\right]r^2 \quad (S\text{-}3)$$

$$A_l = \pi\left[(r+L)^2 - r^2\left(1 + \frac{3}{5}\sigma\frac{L}{r}\right)^{\frac{2}{3}}\right] \quad (S\text{-}4)$$

where $\Omega$ is the solid angle of the interpenetration cone. Therefore, the number of ligands involved in interpenetration ($n_L$) could be calculated using equation S-5 (results in Table S1):

$$n_L = A_0\sigma = 2\pi\sigma\left[1 - \frac{r\left(1 + \frac{3}{5}\sigma\frac{L}{r}\right)^{\frac{1}{3}}}{r+L}\right]r^2 \quad (S\text{-}5)$$

and the average interpenetration depth ($d_i$) could be calculated using equation S-6 (results in Table S1):

$$d_i = \frac{2\Omega}{3}\frac{(r+L)^3}{A_L} - \frac{1}{3}d_{nn} \quad (S\text{-}6)$$

For $IC_{OA}$, the grafting density is 3.38 ligands·nm$^{-2}$, the number of ligands involved in interpenetration and the average interpenetration depth could be calculated as $n_L$=62.3, and $d_i$=0.972 nm. Considering the distance between every other alkyl carbon is 0.254 nm, the average interpenetrating between two nanoparticles is 62.3 ligands with 8 carbons overlapping. Ligand interpenetration provides an opportunity to form local "effective bonding domains" through cooperative hydrocarbon chain interdigitation, which can result in a large van der Waals interactions between them. We label the percentage of hydrocarbon chains involved in "effective bonding domains" (p) and number of methylene unit of a hydrocarbon chain involved in "effective bonding domains" (n). The maximal value of n is determined by the value of di. Then estimated bonding energy is calculated by equation S-7.

$$E_{bonding} = n_L \times p \times n \times E_M \quad (S\text{-}7)$$

where the $E_M$ is the interaction energy between two methylene units from neighboring hydrocarbon chains. $E_M$ was reported as 4.2 meV for two methylene group at 0.49 nm apart in vacuum.[7] The estimated numbers are listed in Table S2.

REFERENCES FOR THE SUPPORTING
INFORMATION OF EXAMPLE 5

[1] J. Park, K. An, Y. Hwang, J. E. Park, H. J. Noh, J. Y. Kim, J. H. Park, N. M. Hwang, T. Hyeon, *Nat. Mater.* 2004, 3, 891.

[2] A. Dong, J. Chen, P. M. Vora, J. M. Kikkawa, C. B. Murray, *Nature* 2010, 466, 474.

[3] D. Benoit, H. Zhu, M. H. Lilierose, R. A. Verm, N. Ali, A. N. Morrison, J. D. Fortner, C. Avendano, V. L. Colvin, *Anal. Chem.* 2012, 84, 9238.

[4] Y. Jiao, D. Han, Y. Ding, X. Zhang, G. Guo, J. Hu, D. Yang, A. Dong, *Nat. Commun.* 2015, 6, 6420.

[5] D. M. Small, *J Lipid Res.* 1984, 25, 13, 1490.

[6] U. Landman, W. D. Luedtke, Faraday Discuss. 2004, 125, 1.

[7] L. Salem, *J. Chem. Phys.* 1962, 37, 2100.

SUPPLEMENTARY TABLES

TABLE S1

The remaining weight percentage from TGA and ligand coverage of different building blocks.

| | Remaining wt % | Grafting density (ligands · nm$^{-2}$) |
|---|---|---|
| AM | 89.68 | 2.54 |
| fcc$_1$ | 88.15 | 2.87 |
| IC$_{OA}$ | 85.93 | 3.38 |
| fcc$_2$ | 83.02 | 4.07 |

TABLE S2

The estimated interparticle bonding energy based on "effective bonding domain" formed though interdigitation of hydrocarbon chains from neighboring particles under the optimal packing model (expressed in $k_bT$ at 298K). n is the number of methylene units from ligands involved in the formation of "effective bonding domain." p is the percentage of interacting ligands form "effective bonding domains" through interdigitation. $E_{bonding}$ = $n_L \times p \times n \times E_M$, where $E_M$ = 4.20 meV.

| | p | | | |
|---|---|---|---|---|
| n | 20% | 40% | 60% | 80% |
| 2 | 4.07 | 8.15 | 12.2 | 16.3 |
| 3 | 6.11 | 12.2 | 18.3 | 24.4 |
| 4 | 8.15 | 16.3 | 24.4 | 32.6 |
| 5 | 10.2 | 20.4 | 30.5 | 40.7 |
| 6 | 12.2 | 24.4 | 36.7 | 48.9 |

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A single-atom-based catalyst system with single-atom catalytic sites in a controlled hierarchical structure over length scales ranging from macroscopic dimensions down to atomic scales, the single-atom-based catalyst system comprising:
    at least one catalyst structure comprising a first assembly of a plurality of single-atom-catalyst superparticles, further comprising a second assembly of a plurality of single-atom-catalyst nanoparticles;
    wherein each of the single-atom-catalyst nanoparticles comprises a core-shell support structure having a crystalline metal oxide support surface, and one or more single-atom catalysts anchored to the support surface, wherein the density and location of the single-atom catalysts on the support surface are controlled within a 20% variance to provide a highly uniform spatial distribution of single-atom catalysts;

wherein each of the second assembly is a sub-micron-sized superlattice of a plurality of single-atom-catalyst nanoparticles, the superlattice having a second density and a second porosity, wherein the second density is controlled within a 20% variance to provide a single-atom-catalyst superparticle having a precise porosity and a highly uniform spatial distribution of the single-atom catalysts; and wherein the first assembly of single-atom-catalyst superparticles has a first density and a first porosity, wherein the first density of the first assembly is controlled within a 10% variance to provide a catalyst structure having a precise porosity and highly uniform spatial distribution of the single-atom catalysts.

2. The single-atom-based catalyst system of claim 1, comprising two or more catalyst structures.

3. The single-atom-based catalyst system of claim 1, further comprising one or more catalytically-inactive support materials.

4. The single-atom-based catalyst system according to claim 1, wherein at least one of the catalyst structures comprises a single-atom-catalyst nanoparticle having one or more of:
   a core structure comprising a $NiO_x$ or $FeO_x$ nanoparticle lattice structure;
   a shell comprising a support matrix comprising MgO, CaO, $SiO_2$, $FeO_x$, $NiO_x$, $AlO_x$, ZnO, $TiO_x$, graphene, or a combination thereof;
   a single-atom catalyst dopant comprising Sm, Fe, Mn, Na, W, Pt, Sn, or a combination thereof.

5. The single-atom-based catalyst system according to claim 4, wherein at least one of the single-atom-catalyst nanoparticles comprises one or more of: Sm-doped MgO/CaO, Fe-doped $SiO_2$, Mn-doped $SiO_2$, Na—W doped $SiO_2$, Ni-doped $SiO_2$, and Pt—Sn-doped $SiO_2$.

6. The single-atom-based catalyst system according to claim 1, comprising a tandem catalyst structure comprising:
   a first catalyst layer comprising a first catalyst structure; and
   a second catalyst layer in fluid communication with the first catalyst layer, said second catalyst layer comprising a second catalyst structure.

7. The single-atom-based catalyst system of claim 6, wherein the first catalyst layer further comprises one or more of:
   a first support layer comprising a catalytically inactive supporter material that supports the first catalyst structure; and
   a first spacer layer in fluid communication with the second catalyst layer.

8. The single-atom-based catalyst system of claim 7, wherein the second catalyst layer further comprises one or more of:
   a second support layer comprising a catalytically inactive supporter material that supports the first catalyst structure; and
   a second spacer layer.

9. The single-atom-based catalyst system according to claim 8, further comprising one or more of:
   a fluid inlet in fluid communication with the first catalyst layer; and
   a fluid outlet in fluid communication with the second catalyst layer.

10. The single-atom-based catalyst system according to claim 1, comprising a radially-structured tandem catalyst, comprising:
    a cylindrical structure having a longitudinal dimension extending parallel a longitudinal axis from a first end to a second end, and a radial dimension extending radially outward from a longitudinal centerline of the catalyst to an outer surface, said cylindrical structure further comprising:
    a central fluid conduit extending along the longitudinal axis from the first end to the second end and comprising a fluid inlet;
    a first catalyst layer disposed radially outward from the central fluid inlet and in fluid communication with the central fluid inlet and comprising a first catalyst structure;
    a second catalyst layer disposed radially outward from the first spacer layer and in fluid communication with the first spacer layer, said second catalyst layer comprising a second catalyst structure; and
    an outer annulus disposed radially outward from the second catalyst layer and in fluid communication with the second catalyst layer.

11. The single-atom-based catalyst system of claim 10, wherein the first catalyst layer further comprises one or more of:
    a first support layer comprising a catalytically inactive supporter material that supports the first catalyst structure; or
    a first spacer layer disposed radially outward from the first catalyst structure and in fluid communication with the second catalyst layer.

12. The single-atom-based catalyst system of claim 11, wherein the second catalyst layer further comprises one or more of:
    a second support layer comprising a catalytically inactive supporter material that supports the first catalyst structure; and
    a second spacer layer.

13. The single-atom-based catalyst system according to claim 12, further comprising one or more of:
    a fluid inlet in fluid communication with the central fluid conduit; or
    a fluid outlet in fluid communication with the outer annulus.

14. The single-atom-based catalyst system according to claim 13, wherein the first catalyst structure comprises a catalyst for the oxidative coupling of methane (OCM) into ethane.

15. The single-atom-based catalyst system according to claim 14, wherein the second catalyst structure comprises a catalyst for the oxidative dehydrogenation of ethane (ODE) into ethylene.

16. A method for three-dimensional (3D) printing a single-atom-based catalyst system comprising:
    providing a first ink substrate comprising a plurality of positively-charged first single atom-catalyst superparticles;
    providing a second ink substrate comprising a plurality of positively-charged second single-atom-catalyst superparticles;
    providing a support ink substrate comprising a plurality of catalytically inactive supporter particles;
    providing a binder ink substrate comprising a plurality of negatively-charged polymeric binders; and
    selectively depositing with a 3D printing apparatus each of the first ink substrate, the second ink substrate, the support ink substrate, and the binder ink substrate to provide the elements of the single-atom-based catalyst system, wherein the single-atom-based catalyst system comprises at least one catalyst structure comprising a first assembly of a plurality of single-atom-catalyst superparticles, further comprising a second assembly of a plurality of single-atom-catalyst nanoparticles;

wherein each of the single-atom-catalyst nanoparticles comprises a core-shell support structure having a crystalline metal oxide support surface, and one or more single-atom catalysts anchored to the support surface, wherein the density and location of the single-atom catalysts on the support surface are controlled within a 20% variance to provide a highly uniform spatial distribution of single-atom catalysts;

wherein each of the second assembly is a sub-micron-sized superlattice of a plurality of single-atom-catalyst nanoparticles, the superlattice having a second density and a second porosity, wherein the second density is controlled within a 20% variance to provide a single-atom-catalyst superparticle having a precise porosity and a highly uniform spatial distribution of the single-atom catalysts; and wherein the first assembly of single-atom-catalyst superparticles has a first density and a first porosity, wherein the first density of the first assembly is controlled within a 10% variance to provide a catalyst structure having a precise porosity and highly uniform spatial distribution of the single-atom catalysts.

17. A method of converting methane to ethylene, comprising:

providing a single-atom-based catalyst system comprising at least one catalyst structure comprising a first assembly of a plurality of single-atom-catalyst superparticles, further comprising a second assembly of a plurality of single-atom-catalyst nanoparticles, wherein each of the single-atom-catalyst nanoparticles comprises a core-shell support structure having a crystalline metal oxide support surface, and one or more single-atom catalysts anchored to the support surface, wherein the density and location of the single-atom catalysts on the support surface are controlled within a 20% variance to provide a highly uniform spatial distribution of single-atom catalysts;

wherein each of the second assembly is a sub-micron-sized superlattice of a plurality of single-atom-catalyst nanoparticles, the superlattice having a second density and a second porosity, wherein the second density is controlled within a 20% variance to provide a single-atom-catalyst superparticle having a precise porosity and a highly uniform spatial distribution of the single-atom catalysts;

wherein the first assembly of single-atom-catalyst superparticles has a first density and a first porosity, wherein the first density of the first assembly is controlled within a 10% variance to provide a catalyst structure having a precise porosity and highly uniform spatial distribution of the single-atom catalysts; and wherein the single-atom-based catalyst system comprises a tandem catalyst structure comprising a first catalyst layer comprising a first catalyst structure, and a second catalyst layer in fluid communication with the first catalyst layer, said second catalyst layer comprising a second catalyst structure;

introducing a first fluid comprising methane to the single-atom-based catalyst system, passing the first fluid through the first catalyst layer so that at least a portion of the methane contacts the first single-atom catalyst structure, providing a first reaction product comprising ethane, passing the first reaction product through the second catalyst layer so that at least a portion of the ethane contacts the second single-atom catalyst structure, providing a second reaction product comprising ethylene, and withdrawing the second reaction product from the single-atom-based catalyst system.

18. The method of claim 17, further comprising:

introducing oxygen to the catalyst structure to activate the catalyst; and purging substantially all of the oxygen from the catalyst structure.

* * * * *